United States Patent
Shen et al.

(10) Patent No.: US 10,570,425 B2
(45) Date of Patent: Feb. 25, 2020

(54) ENGINEERED CYANOBACTERIUM AND ITS APPLICATION FOR PRODUCING ACETATE

(71) Applicants: National Tsing Hua University, Hsinchu (TW); Chang Chun Plastics Co., Ltd., Taipei (TW); Chang Chun Petrochemical Co., Ltd., Taipei (TW)

(72) Inventors: Roa-Pu Shen, Hsinchu (TW); Wei Lu, Hsinchu (TW)

(73) Assignees: NATIONAL TSING HUA UNIVERSITY, Hsinchu (TW); CHANG CHUN PLASTICS CO., LTD., Taipei (TW); CHANG CHUN PETROCHEMICAL CO., LTD., Taipei (TW)

( * ) Notice: Subject to any disclaimer, the term of this patent is extended or adjusted under 35 U.S.C. 154(b) by 159 days.

(21) Appl. No.: 15/856,817

(22) Filed: Dec. 28, 2017

(65) Prior Publication Data
US 2019/0040424 A1 Feb. 7, 2019

(30) Foreign Application Priority Data

Aug. 2, 2017 (TW) .............................. 106126128 A

(51) Int. Cl.
| | | |
|---|---|---|
| C12P 7/54 | (2006.01) |
| C12N 1/20 | (2006.01) |
| C12N 9/10 | (2006.01) |
| C12N 15/74 | (2006.01) |
| C12N 9/12 | (2006.01) |
| C12N 9/04 | (2006.01) |
| C12N 9/16 | (2006.01) |
| C12N 9/02 | (2006.01) |
| C07K 14/245 | (2006.01) |
| C12N 9/88 | (2006.01) |
| C07K 14/195 | (2006.01) |
| C12N 15/52 | (2006.01) |

(52) U.S. Cl.
CPC .............. *C12P 7/54* (2013.01); *C07K 14/195* (2013.01); *C07K 14/245* (2013.01); *C12N 1/20* (2013.01); *C12N 9/0006* (2013.01); *C12N 9/0008* (2013.01); *C12N 9/1029* (2013.01); *C12N 9/1217* (2013.01); *C12N 9/16* (2013.01); *C12N 9/88* (2013.01); *C12N 15/52* (2013.01); *C12N 15/74* (2013.01); *C12Y 101/01202* (2013.01); *C12Y 102/0101* (2013.01); *C12Y 203/01008* (2013.01); *C12Y 207/02001* (2013.01); *C12Y 301/03011* (2013.01); *C12Y 401/01001* (2013.01); *C12Y 401/02022* (2013.01)

(58) Field of Classification Search
None
See application file for complete search history.

(56) References Cited

PUBLICATIONS

Roberte Carpine et al (Genetic engineering of *Synechocystis* sp.PCC6803 for poly-β-hydroxybutyrate overproduction. Algal Research vol. 25, Jul. 2017. p. 117-127. (Year: 2017).*

Ken W. Lu et al., "Production of acetate from different metabolic node in cyanobacterium Synechococcus elongatus PCC7942", 39th Symposium on Biotechnology for Fuels and Chemicals, May 1-4, 2017.

* cited by examiner

Primary Examiner — Kagnew H Gebreyesus
(74) Attorney, Agent, or Firm — WPAT, PC

(57) ABSTRACT

The present invention provides an engineered cyanobacterium, comprising at least one plasmid selected from three novel pathways to produce acetate, which can convert atmospheric carbon dioxide as a raw material into acetate. The present invention also constructs the expression plasmid for three different transporters specific to acetate to be expressed in cyanobacteria, which comprises putative ABC transporter (AatA), succinate/acetate: proton symporter (SatP) and acetate/glycolate: cation symporter (ActP). Therefore, the engineered cyanobacteria of the present invention can produce 0.58 mg/L to 3.54 mg/L of acetate per hour.

10 Claims, 4 Drawing Sheets
Specification includes a Sequence Listing.

US 10,570,425 B2

ENGINEERED CYANOBACTERIUM AND ITS APPLICATION FOR PRODUCING ACETATE

CROSS-REFERENCE TO RELATED APPLICATION

This application claims priority of Taiwan patent application No. 106126128, filed on Aug. 2, 2017, the content of which is incorporated herein in its entirety by reference.

BACKGROUND OF THE INVENTION

1. Field of the Invention

The present invention relates to a method of producing acetate. Particularly, the present invention relates a method of producing acetate using an engineered cyanobacterium.

2. The Prior Arts

Recently, carbohydrate compounds such as sugar are very common for lots of bio-industrial manufacturing processes to produce a variety of valuable chemicals. However, the cost of the feedstock chemicals account for a major portion in the total production cost. Different from other microorganisms, photosynthetic organisms use $CO_2$ as carbon source. Hence, human can get rid of the feedstock cost. In the meantime, the concerns derived from the over-reliance of non-renewable energy source become more serious. Moreover, as the global warming getting more serious and for pursuing a sustainable future of our planet, it is necessary to efficiently recycle the carbon, $CO_2$. Therefore, the process which is able to couple $CO_2$ fixation with synthetic process through photosynthetic microorganism has become an increasingly important topic in the world.

Cyanobacteria often called blue-green algae include a wide range of photosynthetic prokaryotes. They possess photosynthetic equipment similar to the eukaryote's chloroplast functional and structural features. Cyanobacteria are found in a broad range of environments and grow fast, most cyanobacteria are in fresh water, and few cyanobacteria are in ocean.

Nowadays, acetate is considered as a key intermediate chemical for many industrial uses, for example: industrial production of vinyl acetate polymer, dimethyl terephthalate, acetate ester, cellulose acetate, acetic anhydride, calcium magnesium acetate, detergent, food and wood industries. It is a monomer to produce polyvinyl acetate (PVA) for the former and a starting material to produce artificial perfume and chemistry solution for the latter. Human beings must be very familiar with acetate because of its long history in chemical industries and used as vinegar for a long time. As the increasing demand of acetate in various fields, pyroligneous acid method became a world-wide process until the middle period of twenty century. Nowadays, methanol carboxylation is the dominant industrial route and accounting for over 65% of world-wide capacity. The major source of acetate is derived from petroleum-related routes.

In biological fermentation route, the main bacteria described in documents are *Acetobacter* and Gluconabacter. Both bacteria can survive in high concentration of acetate, and the metabolic pathway is ethanol oxidized to acetaldehyde which further oxidized to acetate. As the concentration of carbon dioxide in the atmosphere continues to increase and the petrochemical fuel supply are in constant fluctuation in recent years, the technologies for synthesizing chemical production from renewable energy source are very important. Although the bio-related route for acetate synthesis only account for 10% of global market, it still is an essential process. Many countries define by laws that vinegar for food must originate from biological process. Hence, development and optimization of bio-related process for acetate is one of the important researches to make a progress in the future.

SUMMARY OF THE INVENTION

A primary objective of the present invention is to provide an engineered cyanobacterium, comprising at least one plasmid selected from the group consisting of:
(1) a plasmid containing pyruvate decarboxylase gene (pdc), and acetaldehyde dehydrogenase B gene (aldB) or 3-hydroxypropionaldehyde dehydrogenase gene (aldH);
(2) a plasmid containing phosphate acetyltransferase gene (pta) or phosphate acetyltransferase gene (eutD), and acetate kinase gene (ackA); and
(3) a plasmid containing acetate kinase gene (ackA), fructose-1,6-biphosphatase gene (fbp) gene and fructose-6-phosphoketolase gene (fpk),
wherein the plasmid is incorporated into a host cyanobacterium chromosome, and fpk is obtained from *Bifidobacterium* strains.

Another objective of the present invention is to provide a method of producing acetate using an engineered cyanobacterium, comprising at least one plasmid in a host cyanobacterium, wherein the plasmid is selected from the group consisting of:
(1) a plasmid containing pyruvate decarboxylase gene (pdc), and acetaldehyde dehydrogenase B gene (aldB) or 3-hydroxypropionaldehyde dehydrogenase gene (aldH);
(2) a plasmid containing phosphate acetyltransferase gene (pta) or phosphate acetyltransferase gene (eutD), and acetate kinase gene (ackA); and
(3) a plasmid containing acetate kinase gene (ackA), fructose-1,6-biphosphatase gene (fbp) and fructose-6-phosphoketolase gene (fpk),
wherein the plasmid is incorporated into a host cyanobacterium chromosome, and fpk is obtained from *Bifidobacterium* strains; the engineered cyanobacteria produce 0.58 mg/L to 3.54 mg/L of acetate per hour.

According to an embodiment of the present invention, the host cyanobacterium is *Synechococcus elongates* sp. PCC 7942.

According to an embodiment of the present invention, the plasmid further contains a transporter gene, and the transporter gene is putative ABC transporter (aatA), succinate/acetate:proton symporter (satP) or acetate/glycolate:cation symporter (actP).

According to an embodiment of the present invention, the pta, the eutD, the aldB and the aldH are obtained from *Escherichia coli*, and the pdc is obtained from *Zymomonas mobilis*.

According to an embodiment of the present invention, the engineered cyanobacterium introduces carbon dioxide in the atmosphere or the exhaust gas into the metabolic pathway.

Accordingly, the present invention uses the cyanobacterium that fixing carbon dioxide in photosynthesis to introduce carbon dioxide in the atmosphere or the exhaust gas into the metabolic pathway, and uses the genes from three metabolic pathways to regulate the cyanobacterium by introducing carbon dioxide and convert into acetate. In addition, the present invention also overexpresses three different transporters: putative ABC transporter (AatA), succinate/acetate: proton symporter (SatP) or acetate/glycolate: cation symporter (ActP) specific to acetate in the engineered cyanobacterium, the transporters can enhance the efficacy of excreting acetate into the extracellular medium. Therefore, the engineered cyanobacterium of the present invention can synthesize 0.58 mg/L to 3.54 mg/L of acetate per hour, which is higher production efficiency in the central metabolism of cyanobacteria.

BRIEF DESCRIPTION OF THE DRAWINGS

For the purpose of illustrating the invention, there are shown in the drawings embodiments which are presently preferred. It should be understood, however, that the invention is not limited to the preferred embodiments shown.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

The present invention is to modify and regulate the chromosomes of cyanobacterium by metabolic engineering techniques and to fix carbon dioxide by photosynthetic bacteria as carbon source for acetate production.

The cyanobacterium used in the method of the present invention is *Synechococcus elongates* sp. PCC 7942, the method is to introduce carbon dioxide in the atmosphere or the exhaust gas into the metabolic pathway of cyanobacterium. The carbon dioxide can be converted into acetate production by the regulation of genes in the plasmid of the present invention.

Example 1

Acetate Production of Metabolic Pathway in the Present Invention

The present invention provides three novel metabolic pathways of acetate production, which can utilize carbon dioxide in the atmosphere to be a material for acetate production. As show in FIG. 1A, three novel metabolic pathways in the present invention can be used to produce acetate:

(1) The first metabolic pathway: introducing pyruvate decarboxylase gene (pdc), and acetaldehyde dehydrogenase B gene (aldB) or 3-hydroxypropionaldehyde dehydrogenase gene (aldH);

(2) The second metabolic pathway: introducing phosphate acetyltransferase (pta) gene or phosphate acetyltransferase gene (eutD), and acetate kinase (ackA) gene; and (3) The third metabolic pathway (non-oxidative glycolysis, NOG): introducing acetate kinase (ackA) gene, fructose-1,6-biphosphatase gene (fbp) and fructose-6-phosphoketolase gene (fpk).

Figure 1A:
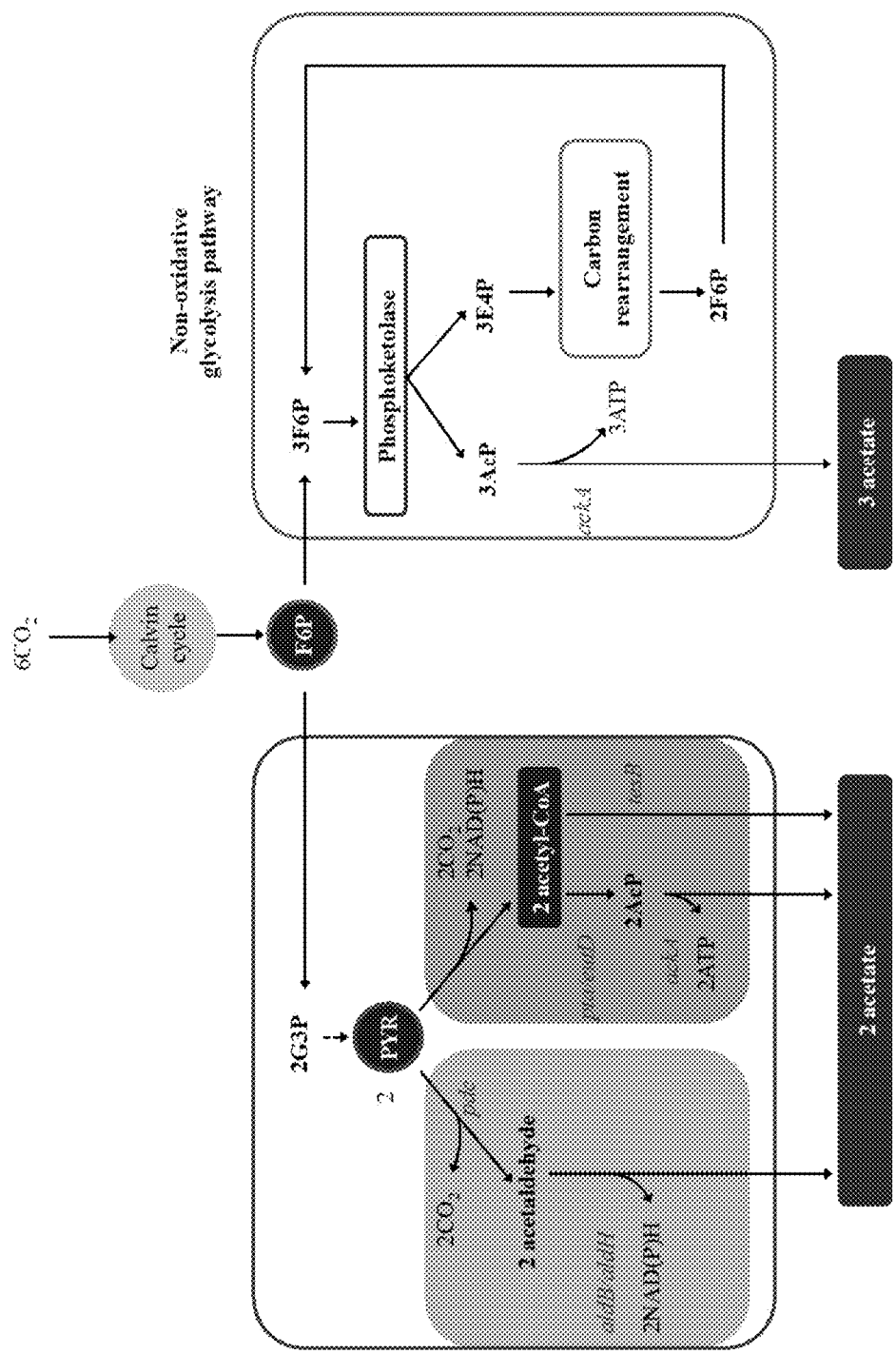
FIG. 1A is a schematic diagram of the three metabolic pathways of the present invention.

Said all the designed metabolic pathways are to use photosynthesis system to produce the reducing power, then, go through to fix carbon in Calvin cycle. The left block as shown in FIG. 1A contains two pathways either directly from pyruvate (PYR), or further from acetyl-coA. The first metabolic pathway forms pyruvate and incorporate it into constructed pathways. Pdc is the key enzyme for production of ethanol in *Zymomonas mobilis* which can efficiently catalyze the reaction from pyruvate to acetaldehyde. The second metabolic pathway is a common enzymes set (Pta/EutD and AckA) for acetate production in *E. coli*. The third metabolic pathway in the right block as shown in FIG. 1A is the pathways from fructorse-6-phosphate (F6P), which is non-oxidative glycolysis (NOG) reaction. Therefore, the engineered cyanobacterium of the present invention can synthesize 0.58 mg/L to 3.54 mg/L of acetate per hour, which is higher production efficiency in the central metabolism of cyanobacteria.

Example 2

Culture Medium and Condition of Cyanobacteria

The cyanobacterium used in the method of the present invention is *Synechococcus elongates* sp. PCC 7942, ATCC 33912. *S. elongates* PCC 7942 strains in the work are gown on BG-11 medium, which is a agar (1.5% w/v) plate containing: 1.5 g/L NaNO$_3$, 0.0272 g/L CaCl$_2$·2H$_2$O, 0.012 g/L ferric ammonium citrate, 0.001 g/L Na$_2$EDTA, 0.040 g/L K$_2$HPO$_4$, 0.0361 g/L MgSO$_4$·7H$_2$O, 0.02 g/L Na$_2$CO$_3$, 1,000× trace mineral (2.86 g/L H$_3$BO$_3$, 1.81 g/L MnCl$_2$·4H$_2$O, 0.222 g/L ZnSO$_4$·7H$_2$O, 0.39 g/L Na$_2$MoO$_4$·2H$_2$O, 0.078 g/L CuSO$_4$·5H$_2$O, 0.049 g/L Co(NO$_3$)$_2$·6H$_2$O), 0.00882 g/L sodium citrate. *S. elongates* PCC 7942 strains are grown in 250 mL screw cap flasks with BG-11 medium which contains 50 mM NaHCO$_3$. Cell growth is measured at OD$_{730}$.

Example 3

Plasmid Construction Containing the Genes Involved in Metabolic Pathway

The present invention introduces the plasmid containing the genes involved in metabolic pathway into neutral site I (NSI) or II (NSII) of *S. elongates* PCC 7942 strains by homologous recombination.

3.1 The Plasmid of the Present Invention

The plasmid construction of the present invention uses pAM2991 (Addgene, Plasmid #40248)(Ivleva et al., EMBO J. 2005 Mar. 23; 24(6):1202-10. Epub 2005 Mar. 10), pAM2991 contains spectinomycin resistance gene, NSI for homologous recombination and Ptrc promoter having 237 bases. The plasmid containing the genes involved in metabolic pathway for acetate is incorporated into *S. elongates* PCC 7942 strains to express by homologous recombination. In addition, the recombinant plasmid is constructed in *Escherichia coli* XL-1 blue strain for propagation.

3.2 Constructing a Plasmid Containing Ptrc Promotor

Amplification of Ptrc promotor: said pAM2991 is as a template for amplification by polymerase chain reaction (PCR) using the primer sets to obtain Ptrc promotor, spectinomycin resistance gene and genes for homologous recombination. The present invention divides the template into two fragments for amplification due to a longer template length (7469 bases), the forward primer SEQ ID NO: 1 and the reverse primer SEQ ID NO: 2 of the first fragment are used to amplify a sequence of 3315 bases (SEQ ID NO: 3). The forward primer SEQ ID NO: 4 and the reverse primer SEQ ID NO: 5 of the second fragment are used to amplify a sequence of 4154 bases (SEQ ID NO: 6).

Recovering the fragments from PCR amplification. The recovering fragment is constructed by DNA assembly method (Enzymatic assembly of DNA molecules up to several hundred kilobases (Gibson et al., Nature Methods 6, 343-345 (2009)) to obtain a recombinant Ptrc plasmid.

3.3 Constructing a Plasmid Containing Pyruvate Decarboxylase Gene (pdc), and Acetaldehyde Dehydrogenase B Gene (aldB) or 3-Hydroxypropionaldehyde Dehydrogenase Gene (aldH)

Amplification of pdc: preparing *Zymomonas mobilis* ATCC 10988 genomic DNA by a routine method, amplifying *Zymomonas mobilis* genomic DNA by PCR using the primer sets to obtain pdc, wherein the forward primer SEQ ID NO: 7 and the reverse primer SEQ ID NO: 8 of pdc are used to amplify a sequence of 1707 bases (SEQ ID NO: 9).

Amplification of aldB: preparing *Escherichia coli* JCL16 genomic DNA (BW25113/F' [traD36 proAB+ lacIqZΔM15 (Tetr)]) by a routine method, amplifying *Escherichia coli* genomic DNA by PCR using the primer sets to obtain aldB, wherein the forward primer SEQ ID NO: 10 and the reverse primer SEQ ID NO: 11 of aldB are used to amplify a sequence of 1539 bases (SEQ ID NO: 12).

Amplification of aldH: preparing *Escherichia coli* JCL16 genomic DNA (BW25113/F' [traD36 proAB+ lacIqZΔM15 (Tetr)]) by a routine method, amplifying *Escherichia coli* genomic DNA by PCR using the primer sets to obtain aldH, wherein the forward primer SEQ ID NO: 13 and the reverse primer SEQ ID NO: 14 of aldH are used to amplify a sequence of 1488 bases (SEQ ID NO: 15).

Figure 1B:
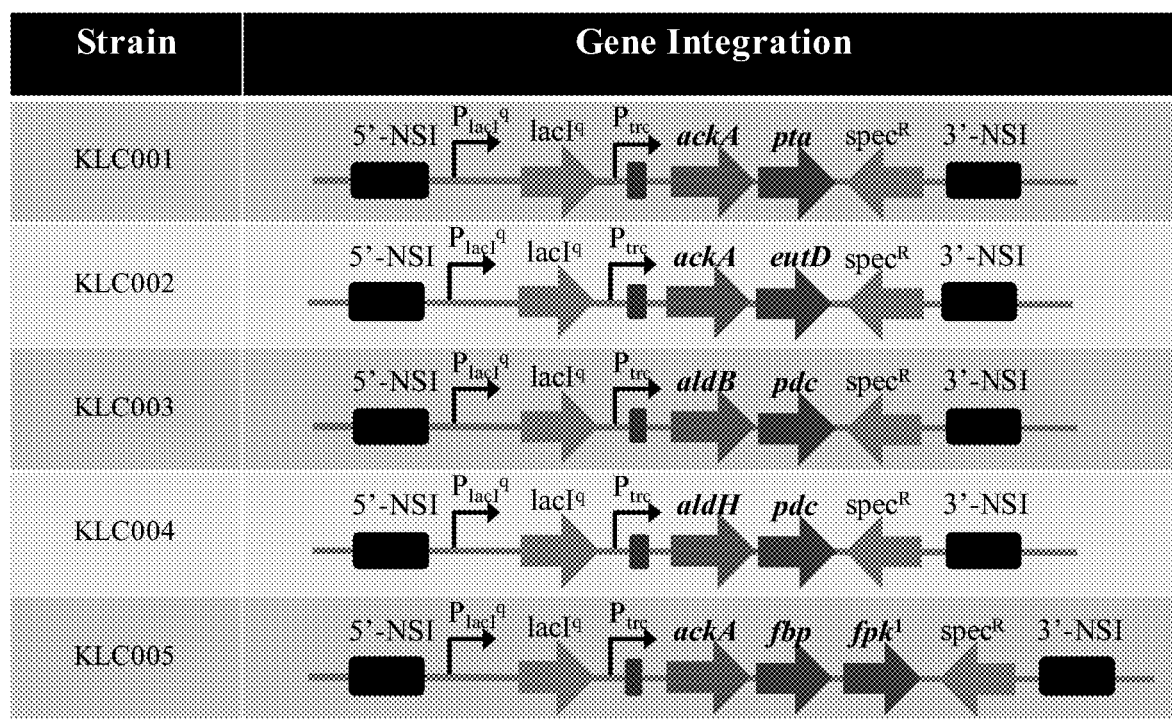
FIG. 1B is a schematic diagram of the engineered cyanobacterium containing plasmid of the present invention; fpk[1] represents fpk is obtained from *Bifidobacterium adolescentis* ATCC 15703.

After amplification, the present invention respectively obtains the recombinant Ptrc-aldB-pdc and the recombinant Ptrc-aldH-pdc using plasmid template and amplification fragments by DNA assembly method. As shown in KLC003 strain of FIG. 1B, the recombinant Ptrc-aldB-pdc mediates homologous recombination with neutral sites of *S. elongates* sp. PCC 7942 to introduce the genes involved in the first metabolic pathway into *S. elongates* sp. PCC 7942 genome. As shown in KLC004 strain of FIG. 1B, the recombinant Ptrc-aldH-pdc mediates homologous recombination with neutral sites of *S. elongates* sp. PCC 7942 to introduce the genes involved in the first metabolic pathway into *S. elongates* sp. PCC 7942 genome.

3.4 Constructing a Plasmid Containing Phosphate Acetyltransferase Gene (pta) Gene or Phosphate Acetyltransferase Gene (eutD), and Acetate Kinase Gene (ackA)

Amplification of pta: preparing *Escherichia coli* JCL16 genomic DNA (BW25113/F' [traD36 proAB+ lacIqZΔM15 (Tetr)]) by a routine method, amplifying *Escherichia coli* genomic DNA by PCR using the primer sets to obtain pta, wherein the forward primer SEQ ID NO: 16 and the reverse primer SEQ ID NO: 17 of pta are used to amplify a sequence of 2145 bases (SEQ ID NO: 18).

Amplification of eutD: preparing *Escherichia coli* JCL16 genomic DNA (BW25113/F' [traD36 proAB+ lacIqZΔM15 (Tetr)]) by a routine method, amplifying *Escherichia coli* genomic DNA by PCR using the primer sets to obtain eutD, wherein the forward primer SEQ ID NO: 19 and the reverse primer SEQ ID NO: 20 of eutD are used to amplify a sequence of 1017 bases (SEQ ID NO: 21).

Amplification of ackA: preparing *Escherichia coli* JCL16 genomic DNA (BW25113/F' [traD36 proAB+ lacIqZΔM15 (Tetr)]) by a routine method, amplifying *Escherichia coli* genomic DNA by PCR using the primer sets to obtain ackA, wherein the forward primer SEQ ID NO: 22 and the reverse primer SEQ ID NO: 23 of ackA are used to amplify a sequence of 1203 bases (SEQ ID NO: 24).

After amplification, the present invention respectively obtains the recombinant Ptrc-ackA-pta and the recombinant Ptrc-ackA-eutD using plasmid template and amplification fragments by DNA assembly method. As shown in KLC001 strain of FIG. 1B, the recombinant Ptrc-ackA-pta mediates homologous recombination with neutral sites of *S. elongates* sp. PCC 7942 to introduce the genes involved in the second metabolic pathway into *S. elongates* sp. PCC 7942 genome. As shown in KLC002 strain of FIG. 1B, the recombinant Ptrc-ackA-eutD mediates homologous recombination with neutral sites of *S. elongates* sp. PCC 7942 to introduce the genes involved in the second metabolic pathway into *S. elongates* sp. PCC 7942 genome.

3.5 Constructing a Plasmid Containing Acetate Kinase Gene (ackA), Fructose-1,6-Biphosphatase Gene (fbp) and Fructose-6-Phosphoketolase Gene (fpk)

Amplification of ackA: preparing *Escherichia coli* JCL16 genomic DNA (BW25113/F' [traD36 proAB+ lacIqZΔM15 (Tetr)]) by a routine method, amplifying *Escherichia coli* genomic DNA by PCR using the primer sets to obtain ackA, wherein the forward primer SEQ ID NO: 22 and the reverse primer SEQ ID NO: 23 of ackA are used to amplify a sequence of 1203 bases (SEQ ID NO: 24).

Amplification of fbp: preparing *Escherichia coli* JCL16 genomic DNA (BW25113/F' [traD36 proAB+ lacIqZΔM15 (Tetr)]) by a routine method, amplifying *Escherichia coli* genomic DNA by PCR using the primer sets to obtain fbp, wherein the forward primer SEQ ID NO: 28 and the reverse primer SEQ ID NO: 29 of fbp are used to amplify a sequence of 999 bases (SEQ ID NO: 30).

Amplification of fpk: preparing *Bifidobacterium adolescentis* ATCC 15703 genomic DNA by a routine method, amplifying *Bifidobacterium adolescentis* 15703 genomic DNA by PCR using the primer sets to obtain fpk (B.A.), wherein the forward primer SEQ ID NO: 31 and the reverse primer SEQ ID NO: 33 of fpk (B.A.) are used to amplify a sequence of 2478 bases (SEQ ID NO: 35).

After amplification, the present invention obtains the recombinant Ptrc-ackA-fbp-fpk (B.A.) using plasmid template and amplification fragments by DNA assembly method. As shown in KLC005 strain of FIG. 1B, the recombinant Ptrc-ackA-fbp-fpk (B.A.) mediates homologous recombination with neutral sites of *S. elongates* sp. PCC 7942 to introduce the genes involved in the third metabolic pathway into *S. elongates* sp. PCC 7942 genome.

Example 4

Screening the Engineered Cyanobacterium

After completion of plasmids construction, all plasmids will be transformed separately by the procedure of incubation of 300 mL of washed cells at the mid-log phase ($OD_{730}$ of 0.4-0.8) with 2 μg of plasmid DNA for 18-24 h in the dark. The culture liquid will then be spread on BG-11 plates with appropriate antibiotics to select a successful recombination. In this embodiment, we use 20 mg/mL spectinomycin and BG-11 medium in BG-11 agar (1.5% w/v) plates for selection and culture maintenance. Selected colonies grown on BG-11 agar plates will be re-streaked and culture at 30° C. to select a successful recombination.

Example 5

Acetate Production of the Present Invention

The present invention uses loops to inoculate the engineered cyanobacterium of the present invention which growing on a BG-11 agar plate in fresh 40 mL BG-11 with appropriate antibiotics. 1 mM isopropyl β-D-1-Thiogalactopyranoside (IPTG) is used to induce the growing culture at cell density $OD_{730}$ nm of 0.4 to 0.6. 4 mL of growing culture is sampled for cell density and acetate production measurements every 2 days. After sampling, 4 mL of fresh BG-11 with 500 mM $NaHCO_3$, appropriate antibiotics, and IPTG are added back to the culture.

5.1 Acetate Quantification 0.2 mL acetate samples are applied to an Agilent Technologies 1260 infinity HPLC equipped with an auto-sampler (Agilent Technologies) and an Agilent Hi-Plex H column (5 mM $H_2SO_4$, 0.6 mL/min, column temperature at 50° C.). Organic acids are detected using a photodiode array detector at 210 nm. Concentrations are determined by extrapolation from standard curves.

5.2 Acetate Production

Figure 2A:
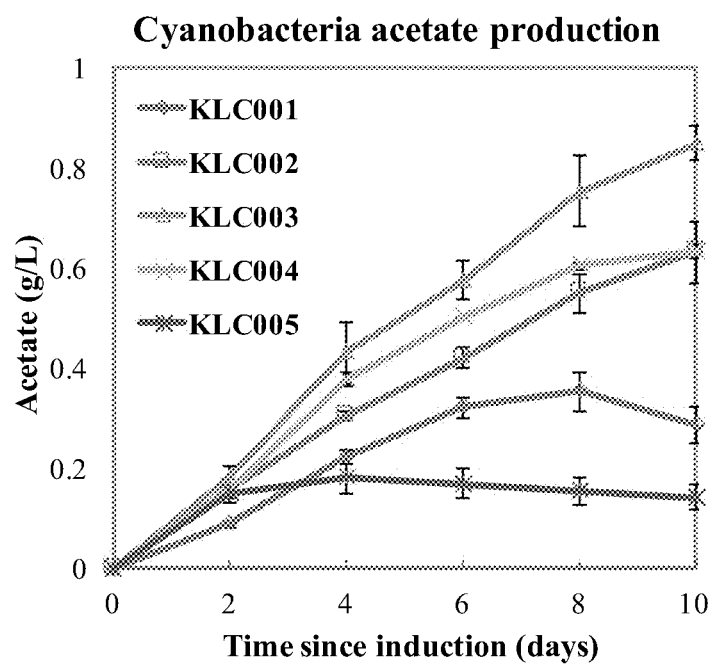
FIG. 2A shows the acetate titer of the engineered cyanobacterium of the present invention.

According to Example 1, the acetate titer over a period of 10 days of the engineered cyanobacterium is shown in FIG. 2A, the acetate titer over a period of 10 days of KLC003 (aldB-pdc) is 0.85 g/L; the acetate titer over a period of 10 days of KLC002 (ackA-eutD) and KLC004 (aldH-pdc) is 0.6 g/L; the acetate titer over a period of 10 days of KLC005 (ackA-fbp-fpk$^1$) is 0.14 g/L; the acetate titer over a period of 8 days of KLC001 (ackA-pta) is 0.35 g/L. Therefore, the engineered cyanobacterium of the present invention can synthesize 0.58 mg/L to 3.54 mg/L of acetate per hour.

Figure 2B:
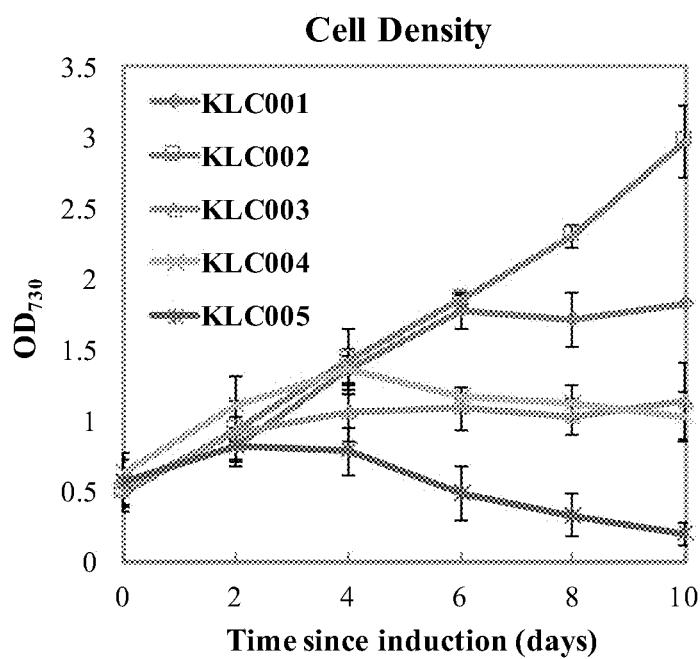
FIG. 2B shows bacteria growth of the engineered cyanobacterium of the present invention.

The present invention also detects bacteria growth using optical density at $OD_{730}$, as shown in FIG. 2B.

For the engineered cyanobacterium containing pta, eutD and ackA, the present invention uses two different phosphate acetyltransferases (Pta and EutD) to substitute CoA group with phosphate group, both genes are from *Escherichia coli* JCL16 genomic DNA (BW25113/F' [traD36 proAB+ lacIqZΔM15 (Tetr)]). Pta-AckA metabolic pathway in *Escherichia coli* is mainly operated when there are excess carbon fluxes in cell especially in rich medium and it will excrete acetate from the Pta-AckA metabolic pathway. Although EutD and Pta both catalyze the transfer of phosphate and acetyl group, they are quite different in efficiency. In Table 1, it shows the enzyme essay of EutD and Pta. Even though they both can catalyze reversible direction of the reaction, the preference of two enzymes is quite different. The $K_{cat}/K_m$ value of EutD for forming acetyl phosphate is much higher than Pta. AckA is responsible for the phosphorylation of ADP to form ATP and is commonly combined with Pta as the acetate synthesis pathway in the cell.

TABLE 1

| Acetyl-CoA forming reaction | | |
|---|---|---|
| | $k_{cat}/K_{mAc-P}(sec^{-1}\mu M^{-1})$ | $k_{cat}/K_{mCoA}(sec^{-1}\mu M^{-1})$ |
| Ec-eutD | 1.3 | 12.6 |
| Ec-pta* | 0.25 | 3.4 |

Bologna, F. P., et al., Characterization of *Escherichia coli* EutD: a phosphotransacetylase of the ethanolamine operon. J Microbiol, 2010. 48(5): p. 629-36.

For the engineered cyanobacterium containing pdc and aldB or aldH, the present invention uses Pdc to catalyze the decarboxylation reaction of pyruvate into acetaldehyde. Some microorganisms have their own pyruvate decarboxylase. For example, yeast and *Zymomonas mobilis*. Yeast is famous for the ability of ethanol production by fermentation. In the fermentation process, pyruvate decarboxylase plays an important role; however, since yeast belongs to eukaryotes, to successfully clone gene from yeast's genome requires more advanced and complicated technics. The present invention uses pyruvate decarboxylase from *Zymomonas mobilis*, the bacterium can utilize glucose efficiently to form pyruvate through Entner-Doudoroff pathway, which then decarboxylated into acetaldehyde by pyruvate decarboxylase and synthesize alcohol. Hence, pyruvate decarboxylase is an important enzyme for efficient ethanol production of *Zymomonas mobilis*.

Aldehyde dehydrogenase catalyze the oxidation reactions of different aldehyde-related chemicals to form their corresponding carboxylic acids by the involvement of reducing power in the cell such as NADH, NADPH as cofactor. The significant roles of aldehyde dehydrogenase in cell's metabolism exist in a wide range of organisms from bacteria to humans. The present invention finds more than ten aldehyde dehydrogenases in *Escherichia coli*, in the reaction, acetaldehyde is substrate for oxidation into acetate. There are a variety of options to choose from, the enzymes react with acetaldehyde even though their substrate specificity is not on acetate. The present invention compares eight aldehyde dehydrogenases kinetic properties using acetaldehyde as substrate, as shown in Table 2 to Table 5, acetaldehyde dehydrogenase B (AldB), 3-hydroxypropionaldehyde dehydrogenase (AldH), succinate semialdehyde dehydrogenase (GabD), phenylacetaldehyde dehydrogenase (PadA), g-aminobutyraldehyde dehydrogenase (AbdH) and lactaldehyde dehydrogenase (ALD) from *E. coli*; and α-ketoglutaric semialdehyde dehydrogenase ($KDH_{ba}$) from *Burkholderia ambifaria* or $KDH_{pp}$ from *Pseudomonas putida* KT2440. After comparison, AldB and AldH from *E. coli* are chosen for cloning. Although ALD and PadA can use acetaldehyde as substrate, but the low preference toward acetaldehyde might affect the reaction. However, AldB and AldH shows a relative higher kinetic property toward acetaldehyde than other substrates.

TABLE 2

| Kinetic properties of aldB | | |
|---|---|---|
| Substrate | $K_m(\mu M)$ | $k_{cat}/K_m(sec^{-1}M^{-1})$ |
| Acetaldehyde | 2.5 | 3750 |
| Chloroacetaldehyde | 3.6 | 3433.3 |
| Propionaldehyde | 5.8 | 650 |

Ho, K. K. and H. Weiner, Isolation and characterization of an aldehyde dehydrogenase encoded by the aldB of *Escherichia coli*. Journal of Bacteriology, 2005. 187(3): p. 1067-1073.

TABLE 3

| Kinetic properties of AldH | | |
| --- | --- | --- |
| Substrate | $K_m$(mM) | $k_{cat}/K_m$(sec$^{-1}$M$^{-1}$) |
| Acetaldehyde | 1 | 11030 |
| 3-Hydroxypropionaldehyde | 0.49 | 58570 |
| Propionaldehyde | 1.21 | 20120 |

Jo, J. E., et al., Cloning, expression, and characterization of an aldehyde dehydrogenase from *Escherichia coli* K-12 that utilizes 3-Hydroxypropionaldehyde as a substrate. Appl Microbiol Biotechnol, 2008. 81(1): p. 51-60.

TABLE 4

| Kinetic properties of padA | | |
| --- | --- | --- |
| Substrate | $K_m$(mM) | $k_{cat}/K_m$(sec$^{-1}$M$^{-1}$) |
| Acetaldehyde | 2.15 | 6750 |
| Benzaldehyde | 0.008 | 20000 |
| Propionaldehyde | 0.0116 | 298333.3 |

Rodriguez-Zavala, J. S., A. Allali-Hassani, and H. Weiner, Characterization of *E. coli* tetrameric aldehyde dehydrogenases with atypical properties compared to other aldehyde dehydrogenases. Protein Sci, 2006. 15(6): p. 1387-96.

TABLE 5

| Kinetic properties of padA | | |
| --- | --- | --- |
| Substrate | $K_m$(mM) | $k_{cat}/K_m$(sec$^{-1}$M$^{-1}$) |
| Acetaldehyde | 15.2 | 40.5 |
| Benzaldehyde | 0.15 | 6283.3 |
| Propionaldehyde | 0.24 | 7666.7 |

Rodriguez-Zavala, J. S., A. Allali-Hassani, and H. Weiner, Characterization of *E. coli* tetrameric aldehyde dehydrogenases with atypical properties compared to other aldehyde dehydrogenases. Protein Sci, 2006. 15(6): p. 1387-96.

For the engineered cyanobacterium containing ackA, fbp and fpk, non-oxidative glycolysis (NOG) has successfully been expressed in *E. coli*. There are several enzymes function in NOG pathway, however, most of the enzymes has been expressed in *Synechococcus elongates* sp. PCC 7942 natively. The present invention overexpresses Fpk form *Bifidobacterium adolescentis* and *Synechococcus elongates* sp. PCC 6803. Furthermore, the present invention overexpresses Fbp which is an irreversible step of carbon rearrangement and play the role of driving force of the pathway.

Example 6

The Engineered Cyanobacterium Containing Transporter

Figure 3:
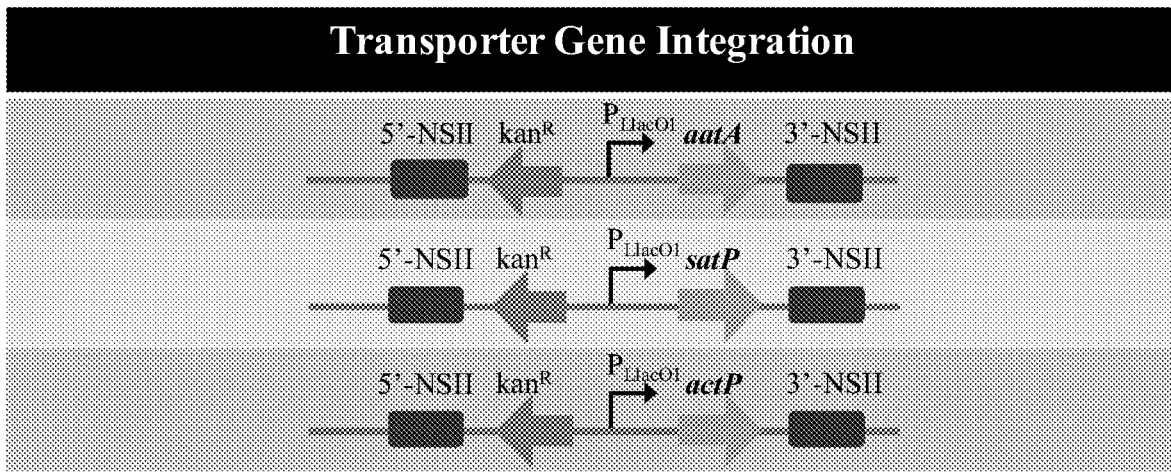
FIG. 3 is a schematic diagram of the engineered cyanobacterium containing transporter plasmid of the present invention.

The present invention also overexpresses three different transporters putative ABC transporter (AatA), succinate/acetate: proton symporter (SatP) and acetate/glycolate: cation symporter (ActP) specific to acetate in the engineered cyanobacterium, as shown in FIG. 3, the transporters can enhance the efficacy of excreting acetate into the extracellular medium. AatA is a putative ABC transpoter in *Acetobacter aceti*. SatP and actP are both from *E. coli*. SatP is a protein symporter which is specific to acetate and succinate. ActP is a protein symporter which is specific to acetate and glycolic acid.

Amplification of aatA: preparing *Acetobacter aceti* ATCC 23746 genomic DNA by a routine method, amplifying *Acetobacter aceti* genomic DNA by PCR using the primer sets to obtain aatA, wherein the forward primer SEQ ID NO: 37 and the reverse primer SEQ ID NO: 38 of aatA are used to amplify a sequence of 1776 bases (SEQ ID NO: 39).

Amplification of satP: preparing *Escherichia coli* JCL16 genomic DNA (BW25113/F' [traD36 proAB+ lacIqZΔM15 (Tetr)]) by a routine method, amplifying *Escherichia coli* genomic DNA by PCR using the primer sets to obtain satP, wherein the forward primer SEQ ID NO: 40 and the reverse primer SEQ ID NO: 41 of satP are used to amplify a sequence of 567 bases (SEQ ID NO: 42).

Amplification of actP: preparing *Escherichia coli* JCL16 genomic DNA (BW25113/F' [traD36 proAB+ lacIqZΔM15 (Tetr)]) by a routine method, amplifying *Escherichia coli* genomic DNA by PCR using the primer sets to obtain actP, wherein the forward primer SEQ ID NO: 43 and the reverse primer SEQ ID NO: 44 of actP are used to amplify a sequence of 1650 bases (SEQ ID NO: 45). As the method in Example 1, the transport genes are cloned into the plasmid.

Comparable Example 1

Comparing Acetate Production of Different Metabolic Pathway

In a engineered cyanobacterium containing acyl-CoA thioesterase 2 (TesB), TesB can remove coenzyme A from both (R)- and (S)-3-hydroxybutyryl-CoA; Furthermore, TesB shows that its substrate specificity doesn't limit to hydroxybutyryl-CoA, acetyl-CoA is an important precursor for bio-synthesis in living organism. Therefore, tesB may be a gene of metabolic pathway to produce acetate. The present invention compares acetate production of the plasmid containing tesB in engineered cyanobacterium.

Amplification of tesB: preparing *Escherichia coli* JCL16 genomic DNA (BW25113/F' [traD36 proAB+ lacIqZΔM15 (Tetr)]) by a routine method, amplifying *Escherichia coli* genomic DNA by PCR using the primer sets to obtain tesB, wherein the forward primer SEQ ID NO: 25 and the reverse primer SEQ ID NO: 26 of tesB are used to amplify a sequence of 861 bases (SEQ ID NO: 27).

Figure 4:
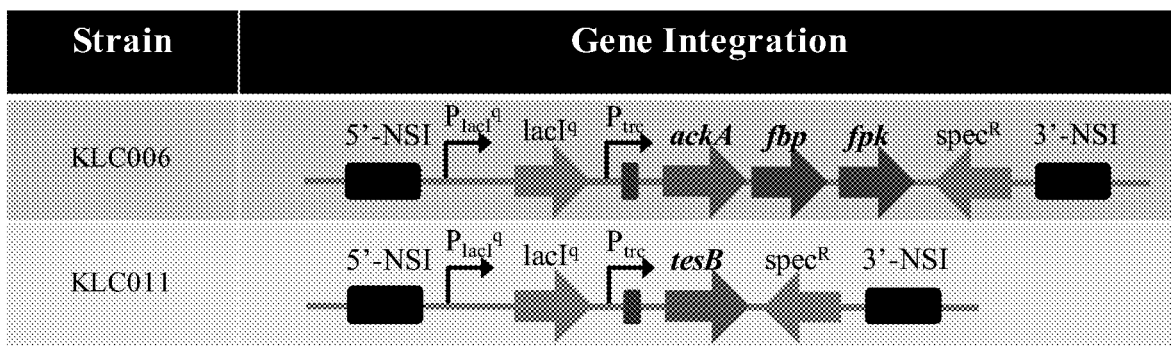
FIG. 4 is a schematic diagram of an engineered cyanobacterium containing other plasmids.

After amplification, the present invention obtains the recombinant Ptrc-tesB using plasmid template and amplification fragments by DNA assembly method. As shown in KLC0011 strain of FIG. 4, the recombinant Ptrc-tesB mediates homologous recombination with neutral sites of *S. elongates* sp. PCC 7942 to introduce the genes involved in the other metabolic pathway into *S. elongates* sp. PCC 7942 genome.

However, the present invention validates that the engineered cyanobacterium containing tesB plasmid fails to produce acetate. Therefore, acetate may not necessarily be produced by a synthetic acetate production pathway.

Comparable Example 2

Comparing fpk from a Different Source

The present invention further compares fpk gene from *Synechocystis* sp. PCC 6803. Preparing *Synechocystis* sp. PCC 6803 genomic DNA by a routine method, amplifying *Synechocystis* sp. PCC 6803 genomic DNA by PCR using the primer sets to obtain fpk, wherein the forward primer SEQ ID NO: 32 and the reverse primer SEQ ID NO: 34 of fpk are used to amplify a sequence of 2418 bases (SEQ ID NO: 36).

After amplification, the present invention obtains the recombinant Ptrc-ackA-fbp-fpk (*Synechocystis* sp. PCC 6803) using plasmid template and amplification fragments by DNA assembly method. As shown in KLC006 strain of FIG. 4, the recombinant Ptrc-ackA-fbp-fpk (*Synechocystis* sp. PCC 6803) mediates homologous recombination with neutral sites of *S. elongates* sp. PCC 7942 to introduce the genes involved in the third metabolic pathway into *S. elongates* sp. PCC 7942 genome.

However, the present invention validates that the engineered cyanobacterium containing Ptrc-ackA-fbp-fpk (*Synechocystis* sp. PCC 6803) plasmid fails to produce acetate. Therefore, acetate may not necessarily be produced by a synthetic acetate production pathway.

In conclusion, the present invention use cyanobacteria regulated by the genes from three metabolic pathways to introduce carbon dioxide and convert into acetate. Therefore, the engineered cyanobacterium of the present invention can synthesize 0.58 mg/L to 3.54 mg/L of acetate per hour.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An engineered cyanobacterium, comprising at least one plasmid selected from the group consisting of:
   (1) a plasmid containing pyruvate decarboxylase gene (pdc), and one of acetaldehyde dehydrogenase B gene (aldB) and 3-hydroxypropionaldehyde dehydrogenase gene (aldH), wherein the pdc gene comprises the sequence of SEQ ID NO:9, the aldB gene comprises the sequence of SEQ ID NO:12, the aldH gene comprises the sequence of SEQ ID NO:15;
   (2) a plasmid containing one of phosphate acetyltransferase gene (pta), phosphate acetyltransferase gene (eutD), and acetate kinase gene (ackA), wherein the pta gene comprises the sequence of SEQ ID NO:18, the eutD gene comprises the sequence of SEQ ID NO:21, the ackA gene comprises the sequence of SEQ ID NO:24; and
   (3) a plasmid containing acetate kinase gene (ackA), fructose-1, 6-biphosphatase gene (fbp) and fructose-6-phosphoketolase gene (fpk), wherein the plasmid is incorporated into a host cyanobacterium chromosome, the fbp gene comprises the sequence of SEQ ID NO:30, and the fpk gene comprises the sequence of SEQ ID NO:35, and fpk is obtained from *Bifidobacterium* strains;
   wherein the engineered cyanobacterium produces 0.58 mg/L to 3.54 mg/L of acetate per hour, and the host cyanobacterium is *Synechococcus elongates* sp. PCC 7942.

2. The engineered cyanobacterium of claim 1, wherein the plasmid further contains a transporter gene.

3. The engineered cyanobacterium of claim 2, wherein the transporter gene is putative ABC transporter gene (aatA), succinate/acetate: proton symporter gene (satP) or acetate/glycolate: cation symporter gene (actP).

4. The engineered cyanobacterium of claim 1, wherein the pta, the eutD, the aldB and the aldH are obtained from *Escherichia coli*.

5. The engineered cyanobacterium of claim 1, wherein the pdc is obtained from *Zymomonas mobilis*.

6. The engineered cyanobacterium of claim 1, which introduces carbon dioxide in the atmosphere or the exhaust gas into the metabolic pathway.

7. A method of producing acetate using an engineered cyanobacterium, comprising at least one plasmid in a host cyanobacterium, wherein the plasmid is selected from the group consisting of:
   (1) a plasmid containing pyruvate decarboxylase gene (pdc), and one of acetaldehyde dehydrogenase B gene (aldB) and 3-hydroxypropionaldehyde dehydrogenase gene (aldH), wherein the pdc gene comprises the sequence of SEQ ID NO:9, the aldB gene comprises the sequence of SEQ ID NO:12, the aldH gene comprises the sequence of SEQ ID NO:15;
   (2) a plasmid containing one of phosphate acetyltransferase gene (pta), phosphate acetyltransferase gene (eutD), and acetate kinase gene (ackA), wherein the pta gene comprises the sequence of SEQ ID NO:18, the eutD gene comprises the sequence of SEQ ID NO:21, the ackA gene comprises the sequence of SEQ ID NO:24; and
   (3) a plasmid containing acetate kinase gene (ackA), fructose-1, 6-biphosphatase gene (fbp) and fructose-6-phosphoketolase gene (fpk), wherein the plasmid is incorporated into a host cyanobacterium chromosome, the fbp gene comprises the sequence of SEQ ID NO:30, the fpk gene comprises the sequence of SEQ ID NO:35, and fpk is obtained from *Bifidobacterium* strains;
   the engineered cyanobacteria produce 0.58 mg/L to 3.54 mg/L of acetate per hour, and the host cyanobacterium is *Synechococcus elongates* sp. PCC 7942.

8. The method of claim 7, wherein the plasmid further contains a transporter gene.

9. The method of claim 8, wherein the transporter gene is putative ABC transporter gene (aatA), succinate/acetate: proton symporter gene (satP) or acetate/glycolate: cation symporter gene (actP).

10. The method of claim 7, wherein the engineered cyanobacterium introduces carbon dioxide in the atmosphere or the exhaust gas into the metabolic pathway.

* * * * *

SEQUENCE LISTING

```
<160> NUMBER OF SEQ ID NOS: 45

<210> SEQ ID NO 1
<211> LENGTH: 25
<212> TYPE: DNA
<213> ORGANISM: Artificial sequence
<220> FEATURE:
<223> OTHER INFORMATION: Synthetic primer

<400> SEQUENCE: 1
cgatcctcta gtatgcttgt aaacc                                               25

<210> SEQ ID NO 2
<211> LENGTH: 27
<212> TYPE: DNA
<213> ORGANISM: Artificial sequence
<220> FEATURE:
<223> OTHER INFORMATION: Synthetic primer

<400> SEQUENCE: 2
accgcctttg agtgagctga taccgct                                             27

<210> SEQ ID NO 3
<211> LENGTH: 3315
<212> TYPE: DNA
<213> ORGANISM: Artificial sequence
<220> FEATURE:
<223> OTHER INFORMATION: Synthetic oligonucleotide

<400> SEQUENCE: 3
cgatcctcta gtatgcttgt aaaccgtttt gtgaaaaaat ttttaaaata aaaaggggga          60
cctctagggt ccccaattaa ttagtaatat aatctattaa aggtcattca aaaggtcatc         120
caccggatca gcttagtaaa gccctcgcta gattttaatg cggatgttgc gattacttcg         180
ccaactattg cgataacaag aaaaagccag cctttcatga tatatctccc aatttgtgta         240
gggcttatta tgcacgctta aaaataataa aagcagactt gacctgatag tttggctgtg         300
agcaattatg tgcttagtgc atctaacgct tgagttaagc cgcgccgcga agcggcgtcg         360
gcttgaacga attgttagac attatttgcc gactaccttg gtgatctcgc ctttcacgta         420
gtggacaaat tcttccaact gatctgcgcg cgaggccaag cgatcttctt cttgtccaag         480
ataagcctgt ctagcttcaa gtatgacggg ctgatactgg gccggcaggc gctccattgc         540
ccagtcggca gcgacatcct tcggcgcgat tttgccggtt actgcgctgt accaaatgcg         600
ggacaacgta agcactacat ttcgctcatc gccagcccag tcgggcggcg agttccatag         660
cgttaaggtt tcatttagcg cctcaaatag atcctgttca ggaaccggat caaagagttc         720
ctccgccgct ggacctacca aggcaacgct atgttctctt gcttttgtca gcaagatagc         780
```

```
cagatcaatg tcgatcgtgg ctggctcgaa gatacctgca agaatgtcat tgcgctgcca    840
ttctccaaat tgcagttcgc gcttagctgg ataacgccac ggaatgatgt cgtcgtgcac    900
aacaatggtg acttctacag cgcggagaat ctcgctctct ccaggggaag ccgaagtttc    960
caaaaggtcg ttgatcaaag ctcgccgcgt tgtttcatca agcctacgg tcaccgtaac    1020 cagcaaatca atatcactgt gtggcttcag gccgccatcc actgcggagc cgtacaaatg    1080
tacggccagc aacgtcggtt cgagatggcg ctcgatgacg ccaactacct ctgatagttg    1140
agtcgatact tcggcgatca ccgcttccct catgatgttt aactttgttt tagggcgact    1200
gccctgctgc gtaacatcgt tgctgctcca taacatcaaa catcgaccca cggcgtaacg    1260
cgcttgctgc ttggatgccc gaggcataga ctgtacccca aaaaacagt cataacaagc    1320 catgaaaacc gccactgcgc cgttaccacc gctgcgttcg gtcaaggttc tggaccagtt    1380
gcgtgagcgc atacgctact tgcattacag cttacgaacc gaacaggctt atgtccactg    1440
ggttcgtgcc ttcatccgtt tccacggtgt gcgtcacccg gcaaccttgg gcagcagcga    1500
agtcgaggca tttctgtcct ggctggcgaa cgagcgcaag gtttcggtct ccacgcatcg    1560
tcaggcattg gcgccttgc tgttcttcta cggcaaggtg ctgtgcacgg atctgccctg    1620
gcttcaggag atcggaagac ctcggccgtc gcggcgcttg ccggtggtgc tgaccccgga    1680
tgaagtggtt cgcatcctcg gttttctgga aggcgagcat cgtttgttcg cccagcttct    1740
gtatggaacg ggcatgcgga tcagtgaggg tttgcaactg cgggtcaagg atctggattt    1800
cgatcacggc acgatcatcg tgcgggaggg caagggctcc aaggatcggg ccttgatgtt    1860
acccgagagc ttggcaccca gcctgcgcga gcaggggaat tgatccggtg gatgacctt    1920 tgaatgacct ttaatagatt atattactaa ttaattgggg accctagagg tccccttttt    1980
tattttaaaa atttttcac aaaacggttt acaagcataa agctctagag tcgacctgca    2040
ggcatgcaag cttcgagtcc ctgctcgtca cgctttcagg caccgtgcca gatatcgacg    2100
tggagtcgat cactgtgatt ggcgaagggg aaggcagcgc tacccaaatc gctagcttgc    2160
tggagaagct gaaacaaacc acgggcattg atctggcgaa atccctaccg ggtcaatccg    2220
actcgcccgc tgcgaagtcc taagagatag cgatgtgacc gcgatcgctt gtcaagaatc    2280
ccagtgatcc cgaaccatag gaaggcaagc tcaatgcttg cctcgtcttg aggactatct    2340
agatgtctgt ggaacgcaca tttattgcca tcaagcccga tggcgttcag cggggttgg    2400 tcggtacgat catcggccgc tttgagcaaa aaggcttcaa actggtgggc ctaaagcagc    2460
tgaagcccag tcgcgagctg gccgaacagc actatgctgt ccaccgcgag cgccccttct    2520
tcaatggcct cgtcgagttc atcacctctg ggccgatcgt ggcgatcgtc ttggaaggcg    2580
aaggcgttgt ggcggctgct cgcaagttga tcggcgctac caatccgctg acggcagaac    2640
cgggcaccat ccgtggtgat tttggtgtca atattggccg caacatcatc catggctcgg    2700
atgcaatcga acagcacaa caggaaattg ctctctggtt tagcccagca gagctaagtg    2760
attggacccc cacgattcaa ccctggctgt acgaataagg tctgcattcc ttcagagaga    2820
cattgccatg cccgtgctgc gatcgcccct ccaagctgcc ttgccccgct gtttcgggct    2880
ggcagccctg gcgttgggc tggcgaccgc ttgccaagaa agcagcgctc cgccggctgc    2940
cggatcgatc ctgcctcgcg cgtttcggtg atgacggtga aaacctctga cacatgcagc    3000
tcccggagac ggtcacagct tgtctgtaag cggatgccgg gagcagacaa gcccgtcagg    3060
gcgcgtcagc gggtgttggc gggtgtcggg gcgcagccat gacccagtca cgtagcgata    3120
```

```
gcggagtgta tactggctta actatgcggc atcagagcag attgtactga gagtgcacca    3180
tatgcggtgt gaaataccgc acagatgcgt aaggagaaaa taccgcatca ggcgctcttc    3240
cgcttcctcg ctcactgact cgctgcgctc ggtcgttcgg ctgcggcgag cggtatcagc    3300
tcactcaaag gcggt                                                     3315
```

```
<210> SEQ ID NO 4
<211> LENGTH: 27
<212> TYPE: DNA
<213> ORGANISM: Artificial Sequence
<220> FEATURE:
<223> OTHER INFORMATION: Synthetic primer

<400> SEQUENCE: 4
agcggtatca gctcactcaa aggcggt                                         27

<210> SEQ ID NO 5
<211> LENGTH: 32
<212> TYPE: DNA
<213> ORGANISM: Artificial sequence
<220> FEATURE:
<223> OTHER INFORMATION: Synthetic primer

<400> SEQUENCE: 5
ggtatatctc ctgtgtgaaa ttgttatccg ct                                   32

<210> SEQ ID NO 6
<211> LENGTH: 4154
<212> TYPE: DNA
<213> ORGANISM: Artificial Sequence
<220> FEATURE:
<223> OTHER INFORMATION: Synthetic oligonucleotide

<400> SEQUENCE: 6
agcggtatca gctcactcaa aggcggtaat acggttatcc acagaatcag gggataacgc    60
aggaaagaac atgtgagcaa aaggccagca aaaggccagg aaccgtaaaa aggccgcgtt    120
gctggcgttt ttccataggc tccgccccc tgacgagcat cacaaaaatc gacgctcaag    180
tcagaggtgg cgaaacccga caggactata aagataccag gcgtttcccc ctggaagctc    240
cctcgtgcgc tctcctgttc cgaccctgcc gcttaccgga tacctgtccg cctttctccc    300
ttcgggaagc gtggcgcttt ctcatagctc acgctgtagg tatctcagtt cggtgtaggt    360
cgttcgctcc aagctgggct gtgtgcacga accccccgtt cagcccgacc gctgcgcctt    420
atccggtaac tatcgtcttg agtccaaccc ggtaagacac gacttatcgc cactggcagc    480
agccactggt aacaggatta gcagagcgag gtatgtaggc ggtgctacag agttcttgaa    540
gtggtggcct aactacggct acactagaag gacagtattt ggtatctgcg ctctgctgaa    600
gccagttacc ttcggaaaaa gagttggtag ctcttgatcc ggcaaacaaa ccaccgctgg    660
tagcggtggt ttttttgttt gcaagcagca gattacgcgc agaaaaaaag gatctcaaga    720
agatcctttg atcttttcta cggggtctga cgctcagtgg aacgaaaact cacgttaagg    780
gattttggtc atgagattat caaaaaggat cttcacctag atccttttaa attaaaaatg    840
aagttttaaa tcaatctaaa gtatatatga gtaaacttgg tctgacagtt accaatgctt    900
aatcagtgag gcacctatct cagcgatctg tctatttcgt tcatccatag ttgcctgact    960
ccccgtcgtg tagataacta cgatacggga gggcttacca tctggcccca gtgctgcaat    1020
gataccgcga gacccacgct caccggctcc agatttatca gcaataaacc agccagccgg    1080
aagggccgag cgcagaagtg gtcctgcaac tttatccgcc tccatccagt ctattaattg    1140
```

```
ttgccgggaa gctagagtaa gtagttcgcc agttaatagt ttgcgcaacg ttgttgccat    1200
tgctgcaggc atcgtggtgt cacgctcgtc gtttggtatg gcttcattca gctccggttc    1260
ccaacgatca aggcgagtta catgatcccc catgttgtgc aaaaaagcgg ttagctcctt    1320
cggtcctccg atcgttgtca gaagtaagtt ggccgcagtg ttatcactca tggttatggc    1380
agcactgcat aattctctta ctgtcatgcc atccgtaaga tgcttttctg tgactggtga    1440
gtcgccgggg ctggcagctt agtcctgcgc aatctctact acatctgcca acccagtgaa    1500
attttgatct ttgctggcag tagtcgccgc agtagtgatg gccgccgagt tggctatcgc    1560
ttggtcaagg gcggcagcag cctgcgggta cctctgctgg aaaaagcgct ccgcatggat    1620
ctgaccaaca tgatcattga gttgcgcgtt tccaatgcct tctccaaggg cggcattccc    1680
ctgactgttg aaggcgttgc caatatcaag attgctgggg aagaaccgac catccacaac    1740
gcgatcgagc ggctgcttgg caaaaaccgt aaggaaatcg agcaaattgc caaggagacc    1800
ctcgaaggca acttgcgtgg tgttttagcc agcctcacgc cggagcagat caacgaggac    1860
aaaattgcct ttgccaaaag tctgctggaa gaggcggagg atgaccttga gcagctgggt    1920
ctagtcctcg atacgctgca agtccagaac atttccgatg aggtcggtta tctctcggct    1980
agtggacgca agcagcgggc tgatctgcag cgagatgccc gaattgctga agccgatgcc    2040
caggctgcct ctgcgatcca aacggccgaa aatgacaaga tcacggccct gcgtcggatc    2100
gatcgcgatg tagcgatcgc ccaagccgag gccgagcgcc ggattcagga tgcgttgacg    2160
cggcgcgaag cggtggtggc cgaagctgaa gcggacattg ctaccgaagt cgctcgtagc    2220
caagcagaac tccctgtgca gcaggagcgg atcaaacagg tgcagcagca acttcaagcc    2280
gatgtgatcg ccccagctga ggcagcttgt aaacgggcga tcgcggaagc gcgggggggcc    2340 gccgcccgta tcgtcgaaga tggaaaagct caagcggaag ggacccaacg gctggcggag    2400
gcttggcaga ccgctggtgc taatgcccgc gacatcttcc tgctccagaa gctcgaaatt    2460
cgagctcggt acccggggat ctgggccgcg ggtcatggct gcgccccgac acccgccaac    2520
acccgctgac gcgccctgac gggcttgtct gctcccggca tccgcttaca gacaagctgt    2580
gaccgtctcc gggagctgca tgtgtcagag gttttcaccg tcatcaccga aacgcgcgag    2640
gcagcagatc aattcgcgcg cgaaggcgaa gcggcatgca tttacgttga caccatcgaa    2700
tggtgcaaaa ccttccgcgg tatggcatga tagcgcccgg aagagagtca attcaggtg    2760 gtgaatgtga aaccagtaac gttatacgat gtcgcagagt atgccggtgt ctcttatcag    2820
accgtttccc gcgtggtgaa ccaggccagc cacgttctg cgaaaacgcg ggaaaaagtg    2880
gaagcggcga tggcggagct gaattacatt cccaaccgcg tggcacaaca actggcgggc    2940
aaacagtcgt tgctgattgg cgttgccacc tccagtctgg ccctgcacgc gccgtcgcaa    3000
attgtcgcgg cgattaaatc tcgcgccgat caactgggtg ccagcgtggt ggtgtcgatg    3060
gtagaacgaa gcggcgtcga agcctgtaaa gcggcggtgc acaatcttct cgcgcaacgc    3120
gtcagtgggc tgatcattaa ctatccgctg atgaccagg atgccattgc tgtggaagct    3180
gcctgcacta atgttccggc gttatttctt gatgtctctg accagacacc catcaacagt    3240 attatttct cccatgaaga cggtacgcga ctgggcgtgg agcatctggt cgcattgggt    3300
caccagcaaa tcgcgctgtt agcgggccca ttaagttctg tctcggcgcg tctgcgtctg    3360 gctgctggg ataaatatct cactcgcaat caaattcagc cgatagcgga acgggaaggc    3420
gactggagtg ccatgtccgg tttttcaacaa accatgcaaa tgctgaatga gggcatcgtt    3480
```

```
cccactgcga tgctggttgc caacgatcag atggcgctgg gcgcaatgcg cgccattacc    3540
gagtccgggc tgcgcgttgg tgcggatatc tcggtagtgg gatacgacga taccgaagac    3600
agctcatgtt atatcccgcc gttaaccacc atcaaacagg attttcgcct gctgggcaa     3660 accagcgtgg accgcttgct gcaactctct cagggccagg cggtgaaggg caatcagctg    3720
ttgcccgtct cactggtgaa agaaaaaacc accctggcgc caatacgca aaccgcctct     3780 ccccgcgcgt tggccgattc attaatgcag ctggcacgac aggtttcccg actgaaagc     3840 gggcagtgag cgcaacgcaa ttaatgtaag ttagcgcgaa ttgatctggt ttgacagctt    3900
atcatcgact gcacggtgca ccaatgcttc tggcgtcagg cagccatcgg aagctgtggt    3960
atggctgtgc aggtcgtaaa tcactgcata attcgtgtcg ctcaaggcgc actcccgttc    4020
tggataatgt tttttgcgcc gacatcataa cggttctggc aaatattctg aaatgagctg    4080
ttgacaatta atcatccggc tcgtataatg tgtggaattg tgagcggata caatttcac    4140 acaggagata tacc                                                    4154

<210> SEQ ID NO 7
<211> LENGTH: 52
<212> TYPE: DNA
<213> ORGANISM: Artificial Sequence
<220> FEATURE:
<223> OTHER INFORMATION: Synthetic primer

<400> SEQUENCE: 7
ggctgttctg aaggagatat accatgagtt atactgtcgg tacctattta gc            52

<210> SEQ ID NO 8
<211> LENGTH: 59
<212> TYPE: DNA
<213> ORGANISM: Artificial Sequence
<220> FEATURE:
<223> OTHER INFORMATION: Synthetic primer

<400> SEQUENCE: 8
tcacaaaacg gtttacaagc atactagagg atcgctagag gagcttgtta acaggctta     59

<210> SEQ ID NO 9
<211> LENGTH: 1707
<212> TYPE: DNA
<213> ORGANISM: Artificial Sequence
<220> FEATURE:
<223> OTHER INFORMATION: Synthetic oligonucleotide

<400> SEQUENCE: 9
atgagttata ctgtcggtac ctatttagcg gagcggcttg tccagattgg tctcaagcat    60
cacttcgcag tcgcgggcga ctacaacctc gtccttcttg acaacctgct tttgaacaaa    120
aacatggagc aggtttattg ctgtaacgaa ctgaactgcg gtttcagtgc agaaggttat    180
gctcgtgcca aggcgcagc agcagccgtc gttacctaca cgtcggtgc gctttccgca     240 tttgatgcta tcggtggcgc ctatgcagaa aaccttccgg ttatcctgat ctccggtgct    300
ccgaacaaca tgatcacgc tgctggtcac gtgttgcatc acgctcttgg caaaaccgac    360
tatcactatc agttggaaat ggccaagaac atcacggccg ccgctgaagc gatttacacc    420
ccggaagaag ctccggctaa atcgatcac gtgattaaaa ctgctcttcg tgagaagaag    480
ccggtttatc tcgaaatcgc ttgcaacatt gcttccatgc cctgcgccgc tcctggaccg    540
gcaagcgcat tgttcaatga cgaagccagc gacgaagctt ctttgaatgc agcggttgaa    600
gaaaccctga aattcatcgc caaccgcgac aaagttgccg tcctcgtcgg cagcaagctg    660
```

```
cgcgcagctg gtgctgaaga agctgctgtc aaatttgctg atgctctcgg tggcgcagtt      720
gctaccatgg ctgctgcaaa aagcttcttc ccagaagaaa acccgcatta catcggcacc      780
tcatggggtg aagtcagcta tccgggcgtt gaaaagacga tgaaagaagc cgatgcggtt      840
atcgctctgg ctcctgtctt caacgactac tccaccactg gttggacgga tattcctgat      900
cctaagaaac tggttctcgc tgaaccgcgt tctgtcgtcg ttaacggcat tcgcttcccc      960
agcgtccatc tgaaagacta tctgacccgt ttggctcaga agtttccaa gaaaaccggt      1020 gctttggact tcttcaaatc cctcaatgca ggtgaactga agaaagccgc tccggctgat      1080
ccgagtgctc cgttggtcaa cgcagaaatc gcccgtcagg tcgaagctct tctgaccccg      1140
aacacgacgg ttattgctga accggtgac tcttggttca atgctcagcg catgaagctc       1200
ccgaacggtg ctcgcgttga atatgaaatg cagtggggtc acattggttg gtctgttcct      1260
gccgccttcg gttatgccgt cggtgctccg gaacgtcgca acatcctcat ggttggtgat      1320
ggttccttcc agctgacggc tcaggaagtc gctcagatgg ttcgcctgaa actgccggtt      1380
atcatcttct tgatcaataa ctatggttac accattgaag ttatgatcca tgatggtccg      1440
tacaacaaca tcaagaactg ggattatgcc ggtctgatgg aagtgttcaa cggtaacggt      1500
ggttatgaca gcggtgctgg taaaggcctg aaggctaaaa ccggtggcga actggcagaa      1560
gctatcaagg ttgctctggc aaacaccgac ggcccaaccc tgatcgaatg cttcatcggt      1620
cgtgaagact gcactgaaga attggtcaaa tggggtaagc gcgttgctgc cgccaacagc      1680
cgtaagcctg ttaacaagct cctctag                                          1707
```

<210> SEQ ID NO 10
<211> LENGTH: 59
<212> TYPE: DNA
<213> ORGANISM: Artificial Sequence
<220> FEATURE:
<223> OTHER INFORMATION: Synthetic primer

<400> SEQUENCE: 10
tgtgagcgga taacaatttc acacaggaga tataccatga ccaataatcc cccttcagc      59

<210> SEQ ID NO 11
<211> LENGTH: 52
<212> TYPE: DNA
<213> ORGANISM: Artificial Sequence
<220> FEATURE:
<223> OTHER INFORMATION: Synthetic primer

<400> SEQUENCE: 11
ccgacagtat aactcatggt atatctcctt cagaacagcc ccaacggttt at             52

<210> SEQ ID NO 12
<211> LENGTH: 1539
<212> TYPE: DNA
<213> ORGANISM: Artificial Sequence
<220> FEATURE:
<223> OTHER INFORMATION: Synthetic oligonucleotide

<400> SEQUENCE: 12
atgaccaata atccccttc agcacagatt aagcccggcg agtatggttt ccccctcaag       60
ttaaaagccc gctatgacaa ctttattggc ggcgaatggg tagcccctgc cgacggcgag      120
tattaccaga atctgacgcc ggtgaccggg cagctgctgt gcgaagtggc gtcttcgggc      180
aaacgagaca tcgatctggc gctggatgct gcgcacaaag tgaaagataa atgggcgcac      240
```

```
acctcggtgc aggatcgtgc ggcgattctg tttaagattg ccgatcgaat ggaacaaaac      300
ctcgagctgt tagcgacagc tgaaacctgg gataacggca aacccattcg cgaaaccagt      360
gctgcggatg taccgctggc gattgaccat ttccgctatt tcgcctcgtg tattcgggcg      420
caggaaggtg ggatcagtga agttgatagc gaaaccgtgg cctatcattt ccatgaaccg      480
ttaggcgtgg tggggcagat tatcccgtgg aacttcccgc tgctgatggc gagctggaaa      540
atggctcccg cgctggcggc gggcaactgt gtggtgctga acccgcacg tcttaccccg       600 cttctgtac tgctgctaat ggaaattgtc ggtgatttac tgccgccggg cgtggtgaac        660
gtggtcaatg cgcaggtgg ggtaattggc gaatatctgg cgacctcgaa acgcatcgcc        720
aaagtggcgt ttaccggctc aacggaagtg ggccaacaaa ttatgcaata cgcaacgcaa      780
aacattattc cggtgacgct ggagttgggc ggtaagtcgc caaatatctt ctttgctgat      840
gtgatggatg aagaagatgc cttttttcgat aaagcgctgg aaggctttgc actgtttgcc     900
tttaaccagg gcgaagtttg cacctgtccg agtcgtgctt tagtgcagga atctatctac      960
gaacgcttta tggaacgcgc catccgccgt gtcgaaagca ttcgtagcgg taacccgctc     1020
gacagcgtga cgcaaatggg cgcgcaggtt tctcacgggc aactggaaac catcctcaac     1080
tacattgata tcggtaaaaa agagggcgct gacgtgctca caggcgggcg cgcaagctg       1140 ctggaaggtg aactgaaaga cggctactac ctcgaaccga cgattctgtt tggtcagaac     1200
aatatgcggg tgttccagga ggagattttt ggcccggtgc tggcggtgac caccttcaaa     1260
acgatggaag aagcgctgga gctggcgaac gatacgcaat atggcctggg cgcgggcgtc     1320
tggagccgca acggtaatct ggcctataag atggggcgcg gcatacaggc tgggcgcgtg     1380
tggaccaact gttatcacgc ttacccggca catgcggcgt ttggtggcta caaacaatca     1440
ggtatcggtc gcgaaaccca caagatgatg ctggagcatt accagcaaac caagtgcctg     1500
ctggtgagct actcggataa accgttgggg ctgttctga                            1539

<210> SEQ ID NO 13
<211> LENGTH: 59
<212> TYPE: DNA
<213> ORGANISM: Artificial Sequence
<220> FEATURE:
<223> OTHER INFORMATION: Synthetic primer

<400> SEQUENCE: 13
tgagcggata caatttcac acaggagata taccatgaat tttcatcatc tggcttact          59

<210> SEQ ID NO 14
<211> LENGTH: 59
<212> TYPE: DNA
<213> ORGANISM: Artificial sequence
<220> FEATURE:
<223> OTHER INFORMATION: Synthetic primer

<400> SEQUENCE: 14
aataggtacc gacagtataa ctcatggtat atctccttca ggcctccagg cttatccag         59

<210> SEQ ID NO 15
<211> LENGTH: 1488
<212> TYPE: DNA
<213> ORGANISM: Artificial Sequence
<220> FEATURE:
<223> OTHER INFORMATION: Synthetic oligonucleotide

<400> SEQUENCE: 15
atgaattttc atcatctggc ttactggcag gataaagcgt taagtctcgc cattgaaaac       60
```

```
cgcttattta ttaacggtga atatactgct gcggcggaaa atgaaaccct tgaaaccgtt    120
gatccggtca cccaggcacc gctggcgaaa attgcccgcg caagagcgt cgatatcgac     180 cgtgcgatga gcgcagcacg cggcgtattt gaacgcggcg actggtcact ctcttctccg    240
gctaaacgta aagcggtact gaataaactc gccgatttaa tggaagccca cgccgaagag    300
ctggcactgc tggaaactct cgacaccggc aaaccgattc gtcacagtct cgtgatgat    360 attcccggcg cggcgcgcgc cattcgctgg tacgccgaag cgatcgacaa agtgtatggc    420
gaagtggcga ccaccagtag ccatgagctg gcgatgatcg tgcgtgaacc ggtcggcgtg    480
attgccgcca tcgtgccgtg gaacttcccg ctgttgctga cttgctggaa actcggcccg    540
gcgctggcgg cgggaaacag cgtgattcta aaaccgtctg aaaaatcacc gctcagtgcg    600
attcgtctcg cggggctggc gaaagaagca ggcttgccgg atggtgtgtt gaacgtggtg    660
acgggttttg gtcatgaagc cgggcaggcg ctgtcgcgtc ataacgatat cgacgccatt    720
gcctttaccg gttcaacccg taccgggaaa cagctgctga agatgcggg cgacagcaac    780 atgaaacgcg tctggctgga agcgggcggc aaaagcgcca acatcgtttt cgctgactgc    840
ccggatttgc aacaggcggc aagcgccacc gcagcaggca tttctacaa ccagggacag    900 gtgtgcatcg ccggaacgcg cctgttgctg aagagagca tcgccgatga attcttagcc    960
ctgttaaaac agcaggcgca aaactggcag ccgggccatc cacttgatcc cgcaaccacc    1020
atgggcacct taatcgactg cgcccacgcc gactcggtcc atagctttat cgggaaggc    1080 gaaagcaaag gcaactgtt gttggatggc cgtaacgccg gctggctgc cgccatcggc    1140 ccgaccatct ttgtggatgt ggacccgaat gcgtccttaa gtcgcgaaga gattttcggt    1200
ccggtgctgg tggtcacgcg tttcacatca gaagaacagg cgctacagct tgccaacgac    1260
agccagtacg gccttggcgc ggcggtatgg acgcgcgacc tctcccgcgc gcaccgcatg    1320
agccgacgcc tgaaagccgg ttccgtcttc gtcaataact acaacgacgg cgatatgacc    1380
gtgccgtttg gcggctataa gcagagcggc aacggtcgcg acaaatccct gcatgccctt    1440
gaaaaattca ctgaactgaa aaccatctgg ataagcctgg aggcctga                  1488

<210> SEQ ID NO 16
<211> LENGTH: 50
<212> TYPE: DNA
<213> ORGANISM: Artificial Sequence
<220> FEATURE:
<223> OTHER INFORMATION: Synthetic primer

<400> SEQUENCE: 16
cctgactgcc tgaaggagat ataccatgtc ccgtattatt atgctgatcc                  50

<210> SEQ ID NO 17
<211> LENGTH: 59
<212> TYPE: DNA
<213> ORGANISM: Artificial Sequence
<220> FEATURE:
<223> OTHER INFORMATION: Synthetic primer

<400> SEQUENCE: 17
tcacaaaacg gtttacaagc atactagagg atcgttactg ctgctgtgca gactgaatc       59

<210> SEQ ID NO 18
<211> LENGTH: 2145
<212> TYPE: DNA
<213> ORGANISM: Artificial Sequence
<220> FEATURE:
```

<223> OTHER INFORMATION: Synthetic oligonucleotide

<400> SEQUENCE: 18

```
atgtcccgta ttattatgct gatccctacc ggaaccagcg tcggtctgac cagcgtcagc      60
cttggcgtga tccgtgcaat ggaacgcaaa ggcgttcgtc tgagcgtttt caaacctatc     120
gctcagccgc gtaccggtgg cgatgcgccc gatcagacta cgactatcgt gcgtgcgaac     180
tcttccacca cgacggccgc tgaaccgctg aaaatgagct acgttgaagg tctgctttcc     240
agcaatcaga aagatgtgct gatggaagag atcgtcgcaa actaccacgc taacaccaaa     300
gacgctgaag tcgttctggt tgaaggtctg gtcccgacac gtaagcacca gtttgcccag     360
tctctgaact acgaaatcgc taaaacgctg aatgcggaaa tcgtcttcgt tatgtctcag     420
ggcactgaca ccccggaaca gctgaaagag cgtatcgaac tgacccgcaa cagcttcggc     480
ggtgccaaaa acaccaacat caccggcgtt atcgttaaca aactgaacgc accggttgat     540
gaacagggtc gtactcgccc ggatctgtcc gagattttcg acgactcttc caaagctaaa     600
gtaaacaatg ttgatccggc gaagctgcaa gaatccagcc cgctgccggt tctcggcgct     660
gtgccgtgga gctttgacct gatcgcgact cgtgcgatcg atatggctcg ccacctgaat     720
gcgaccatca tcaacgaagg cgacatcaat actcgccgcg ttaaatccgt cactttctgc     780
gcacgcagca ttccgcacat gctggagcac ttccgtgccg ttctctgct ggtgacttcc      840
gcagaccgtc ctgacgtgct ggtggccgct tgcctggcag ccatgaacgg cgtagaaatc     900
ggtgccctgc tgctgactgg cggttacgaa atggacgcgc gcatttctaa actgtgcgaa     960
cgtgctttcg ctaccggcct gccggtattt atggtgaaca ccaacacctg gcagacctct    1020
ctgagcctgc agagcttcaa cctggaagtt ccggttgacg atcacgaacg tatcgagaaa    1080
gttcaggaat acgttgctaa ctacatcaac gctgactgga tcgaatctct gactgccact    1140
tctgagcgca gccgtcgtct gtctccgcct gcgttccgtt atcagctgac tgaacttgcg    1200
cgcaaagcgg gcaaacgtat cgtactgccg gaaggtgacg aaccgcgtac cgttaaagca    1260
gccgctatct gtgctgaacg tggtatcgca acttgcgtac tgctgggtaa tccggcagag    1320
atcaaccgtg ttgcagcgtc tcagggtgta gaactgggtg cagggattga aatcgttgat    1380
ccagaagtgg ttcgcgaaag ctatgttggt cgtctggtcg aactgcgtaa gaacaaaggc    1440
atgaccgaaa ccgttgcccg cgaacagctg aagacaacg tggtgctcgg tacgctgatg     1500
ctggaacagg atgaagttga tggtctggtt ccggtgctg ttcacactac cgcaaacacc     1560
atccgtccgc cgctgcagct gatcaaaact gcacccggca gctccctggt atcttccgtg    1620
ttcttcatgc tgctgccgga acaggtttac gtttacggtg actgtgcgat caacccggat    1680
ccgaccgctg aacagctggc agaaatcgcg attcagtccg ctgattccgc tgcggccttc    1740
ggtatcgaac cgcgcgttgc tatgctctcc tactccaccg gtacttctgg tgcaggtagc    1800
gacgtagaaa aagttcgcga agcaactcgt ctggcgcagg aaaaacgtcc tgacctgatg    1860
atcgacggtc cgctgcagta cgacgctgcg gtaatggctc acgttgcgaa atccaaagcg    1920
ccgaactctc cggttgcagg tcgcgctacc gtgttcatct cccggatct gaacaccggt     1980
aacaccacct acaaagcggt acagcgttct gccgacctga tctccatcgg gccgatgctg    2040
cagggtatgc gcaagccggt taacgacctg tcccgtggcg cactggttga cgatatcgtc    2100
tacaccatcg cgctgactgc gattcagtct gcacagcagc agtaa                    2145
```

<210> SEQ ID NO 19
<211> LENGTH: 53

```
<212> TYPE: DNA
<213> ORGANISM: Artificial Sequence
<220> FEATURE:
<223> OTHER INFORMATION: Synthetic primer

<400> SEQUENCE: 19
cgcctgactg cctgaaggag ataccatg attattgaac gttgtcgtga act        53

<210> SEQ ID NO 20
<211> LENGTH: 59
<212> TYPE: DNA
<213> ORGANISM: Artificial Sequence
<220> FEATURE:
<223> OTHER INFORMATION: Synthetic primer

<400> SEQUENCE: 20
cacaaaacgg tttacaagca tactagagga tcgtcattca accagtgttt gtaaactgc    59

<210> SEQ ID NO 21
<211> LENGTH: 1017
<212> TYPE: DNA
<213> ORGANISM: Artificial Sequence
<220> FEATURE:
<223> OTHER INFORMATION: Synthetic oligonucleotide

<400> SEQUENCE: 21
atgattattg aacgttgtcg tgaactggcg ttgcgagcgc cgccagagt ggttttccg     60
gatgcgttag accaacgtgt gctgaaagcc gcgcaatatt tacatcaaca aggtctggca  120
acgcccattc tggtcgccaa tccgtttgaa cttcgtcagt ttgcgctcag tcacggcgtg  180
gcgatggacg ggctacaggt gattgatccg catggcaacc tcgcaatgcg ggaagaattt  240
gctcatcgct ggctggcccg cgcgggcgaa aaaacgccgc cggatgcgct ggaaaaactt  300
accgaccctc tgatgttcgc cgcagcaatg gtcagcgccg gtaaagcgga tgtctgtatc  360
gcgggcaacc tctcttccac ggcaaatgtg ctgcgtgccg gattacgcat tatcggcttg  420
cagccaggct gtaaaacgct ctcttccatt ttcctgatgt tgccacagta cagcggcccg  480
gcgttgggct tgccgattg cagcgtggtg ccacagccga cggcggcgca gctggcggat  540
atcgcgcttg ccagtgccga aacctggcgc gccatcaccg gagaagagcc gcgcgtggcg  600
atgctgtcgt tttccagcaa tggtagcgcc cgtcacccct gtgttgctaa cgtccagcag  660
gcgacagaaa tcgtccgtga gcgcgcacca aagctggtgg tggatggcga gttacagttt  720
gacgccgcct tcgtgccgga agtggcggcg caaaaagcgc ctgccagccc gctacagggc  780
aaggccaatg tgatggtttt tccgtcgctg aagccggaa atattggtta caaaatcgca  840
caacgactcg gcggatatcg tgccgtcggg ccactgatac aaggacttgc cgcgccgatg  900
cacgatctct ctcgtggttg tagcgtgcag gaaattatcg agctggcgct ggtggcagct  960
gtgccgcgtc agacagaagt gaaccgcgaa agcagtttac aaacactggt tgaatga     1017

<210> SEQ ID NO 22
<211> LENGTH: 59
<212> TYPE: DNA
<213> ORGANISM: Artificial Sequence
<220> FEATURE:
<223> OTHER INFORMATION: Synthetic primer

<400> SEQUENCE: 22
gagcggataa caatttcaca caggagatat accatgtcga gtaagttagt actggttct    59

<210> SEQ ID NO 23
```

```
<211> LENGTH: 50
<212> TYPE: DNA
<213> ORGANISM: Artificial Sequence
<220> FEATURE:
<223> OTHER INFORMATION: Synthetic primer

<400> SEQUENCE: 23
cataataata cgggacatgg tatatctcct tcaggcagtc aggcggctcg                50

<210> SEQ ID NO 24
<211> LENGTH: 1203
<212> TYPE: DNA
<213> ORGANISM: Artificial Sequence
<220> FEATURE:
<223> OTHER INFORMATION: Synthetic oligonucleotide

<400> SEQUENCE: 24
atgtcgagta agttagtact ggttctgaac tgcggtagtt cttcactgaa atttgccatc        60
atcgatgcag taaatggtga agagtacctt tctggtttag ccgaatgttt ccacctgccc       120
gaagcacgta tcaaatggaa aatggacggc aataaacagg aagcggcttt aggtgcaggc       180
gccgctcaca gcgaagcgct caactttatc gttaatacta ttctggcaca aaaaccagaa       240
ctgtctcgcg agctgactgc tatcggtcac cgtatcgtac acggcggcga aaagtatacc       300
agctccgtag tgatcgatga gtctgttatt cagggtatca agatgcagc ttcttttgca        360 ccgctgcaca cccggctca cctgatcggt atcgaagaag ctctgaaatc tttcccacag        420
ctgaaagaca aaacgttgc tgtatttgac accgcgttcc accagactat gccggaagag        480
tcttacctct acgccctgcc ttacaacctg tacaaagagc acggcatccg tcgttacggc       540
gcgcacggca ccagccactt ctatgtaacc caggaagcgg caaaaatgct gaacaaaccg       600
gtagaagaac tgaacatcat cacctgccac ctgggcaacg gtggttccgt ttctgctatc       660
cgcaacggta atgcgttga cacctctatg ggcctgaccc cgctggaagg tctggtcatg       720
ggtacccgtt ctggtgatat cgatccggcg atcatcttcc acctgcacga cccctgggc       780 atgagcgttg acgcaatcaa caaactgctg accaaagagt ctggcctgct gggtctgacc       840
gaagtgacca cgactgccg ctatgttgaa gacaactacg cgacgaaaga agacgcgaag       900
cgcgcaatgg acgtttactg ccaccgcctg gcgaaataca tcggtgccta cactgcgctg       960
atggatggtc gtctggacgc tgttgtattc actggtggta tcggtgaaaa tgccgcaatg      1020
gttcgtgaac tgtctctggg caaactgggc gtgctgggct ttgaagttga tcatgaacgc      1080
aacctggctg cacgtttcgg caaatctggt ttcatcaaca agaaggtac ccgtcctgcg       1140 gtggttatcc caaccaacga agaactggtt atcgcgcaag acgcgagccg cctgactgcc      1200
tga                                                                   1203

<210> SEQ ID NO 25
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 25
tgagcggata acaatttcac acaggagata taccatgagt caggcgctaa aaaatttac       59

<210> SEQ ID NO 26
<211> LENGTH: 59
<212> TYPE: DNA
<213> ORGANISM: Artificial Sequence
```

<220> FEATURE:
<223> OTHER INFORMATION: Synthetic primer

<400> SEQUENCE: 26
tcacaaaacg gtttacaagc atactagagg atcgttaatt gtgattacgc atcacccct    59

<210> SEQ ID NO 27
<211> LENGTH: 861
<212> TYPE: DNA
<213> ORGANISM: Artificial Sequence
<220> FEATURE:
<223> OTHER INFORMATION: Synthetic oligonucleotide

<400> SEQUENCE: 27
atgagtcagg cgctaaaaaa tttactgaca ttgttaaatc tggaaaaaat tgaggaagga    60
ctctttcgcg gccagagtga agatttaggt ttacgccagg tgtttggcgg ccaggtcgtg   120
ggtcaggcct tgtatgctgc aaaagagacc gtccctgaag agcggctggt acattcgttt   180
cacagctact ttcttcgccc tggcgatagt aagaagccga ttatttatga tgtcgaaacg   240
ctgcgtgacg gtaacagctt cagcgcccgc cgggttgctg ctattcaaaa cggcaaaccg   300 atttttttata tgactgcctc tttccaggca ccagaagcgg gttcgaaaca tcaaaaaaca   360
atgccgtccg cgccagcgcc tgatggcctc ccttcggaaa cgcaaatcgc caatcgctg    420 gcgcacctgc tgccgccagt gctgaaagat aaattcatct gcgatcgtcc gctgaagtc    480 cgtccggtgg agtttcataa cccactgaaa ggtcacgtcg cagaaccaca tcgtcaggtg   540
tggatccgcg caaatggtag cgtgccggat gacctgcgcg ttcatcagta tctgctcggt   600
tacgcttctg atcttaactt cctgccggta gctctacagc cgcacggcat cggttttctc   660
gaaccgggga ttcagattgc caccattgac cattccatgt ggttccatcg cccgtttaat   720
ttgaatgaat ggctgctgta tagcgtggag agcacctcgg cgtccagcgc acgtggcttt   780
gtgcgcggtg agtttttatac ccaagacggc gtactggttg cctcgaccgt tcaggaaggg   840
gtgatgcgta atcacaatta a                                              861

<210> SEQ ID NO 28
<211> LENGTH: 59
<212> TYPE: DNA
<213> ORGANISM: Artificial Sequence
<220> FEATURE:
<223> OTHER INFORMATION: Synthetic primer

<400> SEQUENCE: 28
cgcgagccgc ctgactgcct gaaggagata taccatgaaa acgttaggtg aatttattg    59

<210> SEQ ID NO 29
<211> LENGTH: 59
<212> TYPE: DNA
<213> ORGANISM: Artificial Sequence
<220> FEATURE:
<223> OTHER INFORMATION: Synthetic primer

<400> SEQUENCE: 29
aggggtgcca ataacaggac tcgtcatggt atatctcctt tacgcgtccg ggaactcac    59

<210> SEQ ID NO 30
<211> LENGTH: 999
<212> TYPE: DNA
<213> ORGANISM: Artificial Sequence
<220> FEATURE:
<223> OTHER INFORMATION: Synthetic oligonucleotide

```
<400> SEQUENCE: 30
atgaaaacgt taggtgaatt tattgtcgaa aagcagcacg agtttctca tgctaccggt      60 gagctcactg ctttgctgtc ggcaataaaa ctgggcgcca agattatcca tcgcgatatc    120
aacaaagcag gactggttga tatcctgggt gccagcggtg ctgagaacgt gcagggcgag    180
gttcagcaga aactcgactt gttcgctaat gaaaaactga agccgcact gaaagcacgc     240 gatatcgttg cgggcattgc ctctgaagaa gaagatgaga ttgtcgtctt tgaaggctgt    300
gaacacgcaa atacgtggt gctgatggac ccctggatg gctcgtccaa catcgatgtt      360
aacgtctctg tcggtaccat tttctccatc taccgccgcg ttacgcctgt tggcacgccg    420
gtaacggaag aagatttcct ccagcctggt aacaaacagg ttgcggcagg ttacgtggta    480
tacggctcct ctaccatgct ggtttacacc accggatgcg gtgttcacgc ctttacttac    540
gatccttcgc tcggcgtttt ctgcctgtgc caggaacgga tgcgcttccc ggagaaaggc    600
aaaacctact ccatcaacga aggaaactac attaagtttc cgaacggggt gaagaagtac    660
attaaattct gccaggaaga agataaatcc accaaccgcc cttatacctc acgttatatc    720
ggttcactgg tcgcggattt ccaccgtaac ctgctgaaag gcggtattta tctctaccca    780
agcaccgcca gccaccccgga cggcaaactg cgtttgctgt atgagtgcaa cccgatggca    840
ttcctggcgg aacaagcggg cggtaaagcg agcgatggca agagcgtat tctggatatc      900 atcccggaaa ccctgcacca cgccgttca ttctttgtcg caacgacca tatggttgaa      960 gatgtcgaac gctttatccg tgagttcccg gacgcgtaa                           999

<210> SEQ ID NO 31
<211> LENGTH: 59
<212> TYPE: DNA
<213> ORGANISM: Artificial Sequence
<220> FEATURE:
<223> OTHER INFORMATION: Synthetic primer

<400> SEQUENCE: 31
tatccgtgag ttcccggacg cgtaaaggag atataccatg acgagtcctg ttattggca     59

<210> SEQ ID NO 32
<211> LENGTH: 59
<212> TYPE: DNA
<213> ORGANISM: Artificial Sequence
<220> FEATURE:
<223> OTHER INFORMATION: Synthetic primer

<400> SEQUENCE: 32 atttttttcac aaaacggttt acaagcatac tagaggatcg tcactcgtta tcgccagcg    59

<210> SEQ ID NO 33
<211> LENGTH: 59
<212> TYPE: DNA
<213> ORGANISM: Artificial Sequence
<220> FEATURE:
<223> OTHER INFORMATION: Synthetic primer

<400> SEQUENCE: 33
ccgtgagttc ccggacgcgt aaaggagata taccatggtt acatccccct tttcccctta    59

<210> SEQ ID NO 34
<211> LENGTH: 59
<212> TYPE: DNA
<213> ORGANISM: Artificial Sequence
<220> FEATURE:
<223> OTHER INFORMATION: Synthetic primer
```

<400> SEQUENCE: 34 tttttttcaca aaacggttta caagcatact agaggatcgc tagaggggcc agcgccaat         59

<210> SEQ ID NO 35
<211> LENGTH: 2478
<212> TYPE: DNA
<213> ORGANISM: Artificial Sequence
<220> FEATURE:
<223> OTHER INFORMATION: Synthetic oligonucleotide

<400> SEQUENCE: 35

| | | | | | |
|---|---|---|---|---|---|
| atgacgagtc | ctgttattgg | cacccttgg | aagaagctga | acgctccggt | ttccgaggaa | 60 |
| gctatcgaag | gcgtggataa | gtactggcgc | gcagccaact | acctctccat | cggccagatc | 120 |
| tatctgcgta | gcaacccgct | gatgaaggag | cctttcaccc | gcgaagacgt | caagcaccgt | 180 |
| ctggtcggtc | actggggcac | caccccgggc | ctgaacttcc | tcatcggcca | catcaaccgt | 240 |
| ctcattgctg | atcaccagca | gaacactgtg | atcatcatgg | gcccgggcca | cggcggcccg | 300 |
| gctggtaccg | ctcagtccta | cctggacggc | acctacaccg | agtacttccc | gaacatcacc | 360 |
| aaggatgagg | ctggcctgca | gaagttcttc | cgccagttct | cctacccggg | tggcatcccg | 420 |
| tcccactacg | ctccggagac | cccgggctcc | atccacgaag | gcggcgagct | gggttacgcc | 480 |
| ctgtcccacg | cctacggcgc | tgtgatgaac | aacccgagcc | tgttcgtccc | ggccatcgtc | 540 |
| ggcgacggtg | aagctgagac | cggcccgctg | gccaccggct | ggcagtccaa | caagctcatc | 600 |
| aacccgcgca | ccgacggtat | cgtgctgccg | atcctgcacc | tcaacggcta | caagatcgcc | 660 |
| aacccgacca | tcctgtcccg | catctccgac | gaagagctcc | acgagttctt | ccacggcatg | 720 |
| ggctatgagc | cgtacgagtt | cgtcgctggc | ttcgacaacg | aggatcacct | gtcgatccac | 780 |
| cgtcgtttcg | ccgagctgtt | cgagaccgtc | ttcgacgaga | tctgcgacat | caaggccgcc | 840 |
| gctcagaccg | acgacatgac | tcgtccgttc | tacccgatga | tcatcttccg | taccccgaag | 900 |
| ggctggacct | gcccgaagtt | catcgacggc | aagaagaccg | agggctcctg | gcgttcccac | 960 |
| caggtgccgc | tggcttccgc | ccgcgatacc | gaggcccact | cgaggtcct | caagaactgg | 1020 |
| ctcgagtcct | acaagccgga | agagctgttc | gacgagaacg | cgccgtgaa | gccggaagtc | 1080 |
| accgccttca | tgccgaccgg | cgaactgcgc | atcggtgaga | acccgaacgc | caacggtggc | 1140 |
| cgcatccgcg | aagagctgaa | gctgccgaag | ctggaagact | acgaggtcaa | ggaagtcgcc | 1200 |
| gagtacggcc | acggctgggg | ccagctcgag | gccacccgtc | gtctgggcgt | ctacacccgc | 1260 |
| gacatcatca | agaacaaccc | ggactccttc | cgtatcttcg | accggatga | accgcttcc | 1320 |
| aaccgtctgc | aggccgctta | cgacgtcacc | aacaagcagt | gggacgccgg | ctacctgtcc | 1380 |
| gctcaggtcg | acgagcacat | ggctgtcacc | ggccaggtca | ccgagcagct | ttccgagcac | 1440 |
| cagatggaag | gcttcctcga | gggctacctg | ctgaccggcc | gtcacggcat | ctggagctcc | 1500 |
| tatgagtcct | tcgtgcacgt | gatcgactcc | atgctgaacc | agcacgccaa | gtggctcgag | 1560 |
| gctaccgtcc | gcgagattcc | gtggcgcaag | ccgatctcct | ccatgaacct | gctcgtctcc | 1620 |
| tcccacgtgt | ggcgtcagga | tcacaacggc | ttctcccacc | aggatccggg | tgtcacctcc | 1680 |
| gtcctgctga | acaagtgctt | caacaacgat | acgtgatcg | gcatctactt | cccggtggat | 1740 |
| tccaacatgc | tgctcgctgt | ggctgagaag | tgctacaagt | ccaccaacaa | gatcaacgcc | 1800 |
| atcatcgccg | gcaagcagcc | ggccgccacc | tggctgaccc | tggacgaagc | tcgcgccgag | 1860 |
| ctcgagaagg | gtgctgccga | gtggaagtgg | gcttccaacg | tgaagtccaa | cgatgaggct | 1920 |

| | |
|---|---|
| cagatcgtgc tcgccgccac cggtgatgtt ccgactcagg aaatcatggc cgctgccgac | 1980 |
| aagctggacg ccatgggcat caagttcaag gtcgtcaacg tggttgacct ggtcaagctg | 2040 |
| cagtccgcca aggagaacaa cgaggccctc tccgatgagg agttcgctga gctgttcacc | 2100 |
| gaggacaagc cggtcctgtt cgcttaccac tcctatgccc gcgatgtgcg tggtctgatc | 2160 |
| tacgatcgcc cgaaccacga caacttcaac gttcacggct acgaggagca gggctccacc | 2220 |
| accaccccgt acgacatggt tcgcgtgaac aacatcgatc gctacgagct ccaggctgaa | 2280 |
| gctctgcgca tgattgacgc tgacaagtac gccgacaaga tcaacgagct cgaggccttc | 2340 |
| cgtcaggaag ccttccagtt cgctgtcgac aacggctacg atcacccgga ttacaccgac | 2400 |
| tgggtctact ccggtgtcaa caccaacaag cagggtgcta tctccgctac cgccgcaacc | 2460 |
| gctggcgata acgagtga | 2478 |

<210> SEQ ID NO 36
<211> LENGTH: 2418
<212> TYPE: DNA
<213> ORGANISM: Artificial Sequence
<220> FEATURE:
<223> OTHER INFORMATION: Synthetic oligonucleotide

<400> SEQUENCE: 36

| | |
|---|---|
| atggttacat ccccctttc ccttagtccc tttggtcaag ctagatccac cgtcactggc | 60 |
| aatcccttg acccgacaga acttaaccaa atgcacggtt tttggcgggc agccaactac | 120 |
| ttggcagtgg gcatgattta tctgcgggat aatccccttt gcgggaacc gcttcaaccg | 180 |
| gaacagatca agcatcgcct gttgggtcac tggggttcta gtcccggcat tagttttctc | 240 |
| tacacccatc tcaaccgcat tatcaggaaa tttgaccagg atatgctgta catggtgggg | 300 |
| cctggccacg gcgcaccagg cttttttgggg ccctgctacc tagaagggag ctattctcgc | 360 |
| tttttttgccg agtgtagtga agatgaggac ggcatgaagc gcttttttcaa acaattttcc | 420 |
| tttcccggtg gcattggcag tcattgcact cccgaaaccc ctggttccat ccacgagggg | 480 |
| ggagaattgg gctactgcct atcccatgcc tatggcgctg cctttgataa tcccaattta | 540 |
| attgtggtcg gtttagcggg ggatggggag tcggaaacag gccccttggc tacctcctgg | 600 |
| cattccaata agtttattaa cccgattcgg gatggggcag ttttaccggt tctgcatctc | 660 |
| aatgggtaca agattaacaa tccaagtgtt ttatctcgca ttagccatga agaattaaag | 720 |
| gctttatttg aaggttacgg ttataccccc tactttgttg aaggctctga cccggaatct | 780 |
| atgcaccaag cctatgcagc cacgttggat cattgtgtga gcgaaattca tcaaatccaa | 840 |
| caagaagctc gtagtacggg cattgccgtg cgcccccgtt ggcccatggt tgtgatgcgg | 900 |
| actcccaagg gatggacggg gcctgactat gttgatggcc ataaggtaga aggttttggg | 960 |
| cgatcgcacc aagttcccat gggggcatg cacgagaatc cagcccattt gcaacagttg | 1020 |
| gaagcttgga tgcggagtta taagccgaa gaattgttcg acgagcaagg tactttaaaa | 1080 |
| ccgggatttta aggcgatcgc cccggaggga gataagcgtt taggctctac tccctacgcc | 1140 |
| aatggtggtt tgttacggcg gggtttgaaa atgccggact ttcgtcaata tggtattgat | 1200 |
| gtggaccaac caggcaccat cgaagcccct aatactgcac ccctgggagt atttctgcgg | 1260 |
| gatgtgatgg ccaacaacat gaccaatttc cgcctgtttg ccccgatga aaatagttcc | 1320 |
| aataaactcc atgccgtcta cgaggttagc aaaaaattct ggattgctga atatctagaa | 1380 |
| gaagaccagg atgggggga attaagtccc gatggtcggg tgatggaaat gttaagcgag | 1440 |
| cacacccttag aaggttggtt agaggcctat cttttaaccg ggcgtcacgg ctttttcgcc | 1500 |

-continued

```
acctatgaat cctttgccca tgtgatcact tccatggtta accaacacgc taaatggttg    1560
gatatttgtc gacacctcaa ctggcgggca gatatttcct cgttaaatat cttgatgacg    1620
tccaccgtgt ggcgacagga tcacaacggg tttacccacc aagatcccgg ttttctcgat    1680
gtcattctca ataaaagccc cgatgtggtg cgaatttatt taccccccga tgttaattct    1740
ctgctttccg tagcggacca ttgtttacag agcaaaaact acatcaacat catcgtttgc    1800
gataagcaag cccacctgca ataccaggac atgacttccg ctatccgtaa ctgcactaaa    1860
ggggtggaca tttgggaatg ggccagtaat gatgccggta cggaaccgga tgtggtgatg    1920
gcagcggcgg gggatattcc caccaaagag gccttggcgg ccacagccat gctaaggcaa    1980
ttttttccta atctgagaat tcgctttgtc agcgtgattg atttgctcaa actgcaaccg    2040
gaatcggagc atcccatgg cctgagcgat cgggattttg actccctctt taccaccgat    2100
aaaccgatta tttttaactt ccacgcctat ccctggttaa ttcatcggtt gacctatcga    2160
cggactaacc atggcaatct ccatgtgcgg ggctacaagg aaaagggcaa catcaacacc    2220
cccatggatt tagcgattca aaaccagatt gaccgtttca gcctcgccat tgatgtgatc    2280
gatcgcctgc cccaattgcg ggtggccgga gcccacatca aggaaatgct caaggatatg    2340
cagattgact gcaccaacta cgcctacgaa cacggcattg atatgccaga aatcgttaat    2400
tggcgctggc ccctctag                                                  2418
```

<210> SEQ ID NO 37
<211> LENGTH: 59
<212> TYPE: DNA
<213> ORGANISM: Artificial Sequence
<220> FEATURE:
<223> OTHER INFORMATION: Synthetic primer

<400> SEQUENCE: 37

```
aattgtgagc ggataacaat ttcacacagg agatatacca tggcgcatcc tccccttct       59
```

<210> SEQ ID NO 38
<211> LENGTH: 59
<212> TYPE: DNA
<213> ORGANISM: Artificial Sequence
<220> FEATURE:
<223> OTHER INFORMATION: Synthetic primer

<400> SEQUENCE: 38

```
ccgctgtagt acggaccgcg atctcgagga tcggaattct catttccagt tccagccag       59
```

<210> SEQ ID NO 39
<211> LENGTH: 1776
<212> TYPE: DNA
<213> ORGANISM: Artificial Sequence
<220> FEATURE:
<223> OTHER INFORMATION: Synthetic oligonucleotide

<400> SEQUENCE: 39

```
atggcgcatc ctccccttct tcatcttcag gacattactc tttcattagg agggaacccg      60
ctgctggatg gcgccggttt tgccgttggg cgtggtgagc gcctctgcct tgtggggcga     120
aacggttcgg gaaagtccac cctgctcaaa attgctgcgg tgttattca gccagattcg      180 ggtctgtgt ttgtccagcc cggtgcttcc ctgcgctatc tgccgcagga gccggattta     240
agcgcttatg ccacaacggc ggattacgtt gtgggccaga ttgagaccc ggatatggca     300 tggcgcgcca cgccattgct ggatgctctg ggcctgacag gtagggaaag cacgcaaaat     360
```

```
ctttcaggcg gtgaaggtcg gcgttgtgct attgctggtg tattggcggc ggcccccgat    420
gtgctgctgc tggatgagcc caccaaccat ctggatatgc ctaccattga atggttggag    480
cgtgaactgc tgagccttgg cgccatggta attatcagcc atgataggcg gctgctttcc    540
accctttcac gttctgttgt gtggctggat cggggtgtaa cccgcaggct tgatgaagga    600
tttggaaggt ttgaagcctg cgagaggag gttctggaac aggaagagcg tgatgcgcat     660
aaactggacc ggaaaatcgc gcgggaagaa gactggatgc gttatggcgt aacgcgcgc    720 cgcaaacgca atgtacgccg tgtgcgggaa ctagcagatt tgcgcacagc ccgtaaggag    780
gccattcggg cacccggcac ccttaccttg aacacgcagc tgcggccaca tcgcaagctg    840
gtggctgtgg ccgaagatat tagtaaggca tggggtgaaa agcaggttgt tcgccatttg    900
gacctgcgca ttttacgtgg agaccggctt ggtattgtgg gggccaatgg tgcaggcaaa    960
accacattgt tgcggatgct aacagggctg gaccaacccg atagtggcac aatctcactt   1020
ggtccttccc ttaatatggt cacgctggat cagcagcgac gtaccctgaa cccggaacgc   1080
acactagccg ataccttgac agaaggcgga ggcgatatgg tgcaggttgg cacggaaaag   1140
cgccacgttg tggggtatat gaaagacttt ctgtttcggc cagaacaggc acgcacaccc   1200
gtaagtgccc tttctggcgg ggagcgaggg cggttaatgc tggcatgcgc attggccaag   1260
ccctccaacc tgctggtgct ggatgaaccc accaatgatc tggatctgga aacactggat   1320
attttgcaag acatgctcgc cagttgtgaa ggcacagtgc tgcttgtaag ccatgatcgt   1380
gattttctgg atcgggttgc aacatccgtc ttggcgacag agggagatgg caactggata   1440
gaatatgctg gcggatacag tgacatgctg gctcagcggc accagaaacc gttgacaacg   1500
gcctctgtgg tggaaaacga acccacaaaa cccaagagaa caactgctgc gcgtggcccg   1560
accaaaaagc tgagttataa ggaccagttt gcgctgata atctgcccaa ggaaatggaa    1620
aagctggaag cacaggctgc caactgcgtg aaaaactggc agatccagat ttatatggaa   1680 aaaccccgc gcagtttgag aaactttcgg ctgatttaca gaagctcgaa acaaagctgg    1740
cagaatctga agaacgctgg ctggaactgg aaatga                             1776

<210> SEQ ID NO 40
<211> LENGTH: 59
<212> TYPE: DNA
<213> ORGANISM: Artificial Sequence
<220> FEATURE:
<223> OTHER INFORMATION: Synthetic primer

<400> SEQUENCE: 40
gacgcactga ccgaattcat taaagaggag aaaggtacca tgggcaacac taagttggc    59

<210> SEQ ID NO 41
<211> LENGTH: 59
<212> TYPE: DNA
<213> ORGANISM: Artificial Sequence
<220> FEATURE:
<223> OTHER INFORMATION: Synthetic primer

<400> SEQUENCE: 41
actgagcctt tcgttttatt tgatgcctct agcacgcgtt tagtgggatt caccaatcg    59

<210> SEQ ID NO 42
<211> LENGTH: 567
<212> TYPE: DNA
<213> ORGANISM: Artificial Sequence
<220> FEATURE:
<223> OTHER INFORMATION: Synthetic oligonucleotide
```

<400> SEQUENCE: 42

```
atgggcaaca ctaagttggc taatccggca ccgctgggcc tgatgggctt cggcatgacc      60
accattctgc ttaacctgca caacgtgggt tatttcgctc tggacggtat tattcttgcc     120
atgggcattt tctacggcgg catcgcgcaa attttgctg gtctgctgga gtacaaaaaa      180
ggcaacactt tcggtttaac cgcattcacc tcttacggtt ctttctggct gacgctggtt     240
gcgattctgc tgatgccgaa actgggtctg accgatgcgc aaatgcaca gttccttggt      300
gtctacctgg gtctgtgggg cgtatttacg ctgtttatgt tcttcggcac gctgaaaggc     360
gcacgcgttc tgcaattcgt tttctttagc ctgaccgtgc tgtttgccct gctggcgatc     420
ggtaacattg ccggtaacgc cgcaatcatc cactttgccg gctggattgg gctgatctgc     480
ggtgccagcg caatctatct ggcgatgggt gaagtactga acgagcagtt tggtcgcacc     540
gttctgccga ttggtgaatc ccactaa                                         567
```

<210> SEQ ID NO 43
<211> LENGTH: 59
<212> TYPE: DNA
<213> ORGANISM: Artificial Sequence
<220> FEATURE:
<223> OTHER INFORMATION: Synthetic primer

<400> SEQUENCE: 43

```
cgcactgacc gaattcatta agaggagaa aggtaccatg aaaagagttc tgacggcgc       59
```

<210> SEQ ID NO 44
<211> LENGTH: 59
<212> TYPE: DNA
<213> ORGANISM: Artificial Sequence
<220> FEATURE:
<223> OTHER INFORMATION: Synthetic primer

<400> SEQUENCE: 44

```
actgagccctt tcgttttatt tgatgcctct agcacgcgtt taatgcgcgc ggccttgct     59
```

<210> SEQ ID NO 45
<211> LENGTH: 1650
<212> TYPE: DNA
<213> ORGANISM: Artificial Sequence
<220> FEATURE:
<223> OTHER INFORMATION: Synthetic oligonucleotide

<400> SEQUENCE: 45

```
atgaaaagag ttctgacggc gcttgccgcc acactccctt tcgcagctaa cgccgcggat     60
gctattagcg gggccgtaga gcgccagcca acgaactggc aggcgattat tatgttcctg    120
attttcgtcg tgtttacgct cggcattacc tactgggcat caaaacgcgt acgttctcgt    180
agcgactact acaccgcagg cggcaatatc actggcttcc agaacgggct ggcgattgcc    240
ggggactata tgtccgccgc ctcattcttg gggatctccg cgctggtgtt tacctccggc    300
tatgacggct taatttactc gctgggcttc ctggtgggct ggccgatcat tttgttcctg    360
attgccgaac gtctgcgtaa cctggggcgc tacaccttg ccgatgtggc ctcttaccgt    420
ctgaaacaag ggccgattcg tattctttcg gcctgtggtt ctctggtggt ggtggcgctt    480
taccttatcg cccagatggt gggcgcaggt aaactgatcg agctgctgtt tggccttaac    540
tatcacattg cggtggtgct ggtcggcgtg ctgatgatga tgtacgtcct gttcggcggc    600
atgctggcga ccacctgggt gcaaattatc aaagccgtgc tgttgctgtt cggtgccagc    660
```

-continued

```
tttatggcct ttatggtgat gaaacacgtc ggctttagct tcaacaatct gttcagtgaa      720
gcgatggcgg tacacccgaa aggtgtcgac atcatgaagc cgggcgggct ggtgaaagat      780
ccgatctccg cgctctctct gggtctggga ctgatgtttg gtacggcggg cttgccgcac      840
attctgatgc gcttctttac agtcagcgat gcccgcgaag cacgtaagag cgtgttctac      900
gccaccgggt ttatgggcta cttctatatt ctgaccttta ttatcggctt cggcgcgatc      960
atgctggttg gtgcgaatcc ggaatataaa gacgcggcgg gccatctgat tggtggtaac     1020
aacatggcgg ccgttcacct ggcgaatgca gtgggcggca acctgttcct cggttttatt     1080
tcagcggttg ctttcgccac tatcctcgcg gtggttgcgg gtctgacgct ggcgggcgca     1140
tccgcggttt cgcatgactt gtacgctaac gtcttcaaaa aaggcgcgac cgaacgtgaa     1200
gagctgcggt tatcaaaaat caccgtactg atcctcggcg tgattgcgat tatcctcggc     1260
gtgctgtttg agaatcagaa catcgccttt atggtggggc tggcgtttgc catcgcggcg     1320
agctgtaact tcccgatcat tctgctttct atgtactggt cgaaactgac cacgcgtggc     1380
gcgatgatgg gtggctggct ggggctgatt accgcagtag tactgatgat cctcggcccg     1440
acgatttggg tacagatcct tggtcacgaa aaagccatct tcccgtatga atacccggcg     1500
ctgttctcta tcaccgtggc attcctcggc atctggttct tctcggcaac cgataactca     1560
gcggaaggcg cgcgtgagcg tgaactgttc cgcgcgcagt ttatccgctc ccagaccggc     1620
tttggcgttg agcaaggccg cgcgcattaa                                      1650
```